US006495671B1

(12) United States Patent
Manoharan et al.

(10) Patent No.: US 6,495,671 B1
(45) Date of Patent: Dec. 17, 2002

(54) OLIGONUCLEOTIDE AND NUCLEOTIDE AMINE ANALOGS, METHODS OF SYNTHESIS AND USE

(75) Inventors: Muthiah Manoharan, Carlsbad; P. Dan Cook, San Marcos, both of CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/689,964

(22) Filed: Oct. 12, 2000

Related U.S. Application Data

(60) Division of application No. 08/397,277, filed as application No. PCT/US93/08367 on Sep. 3, 1993, now Pat. No. 6,235,886, which is a continuation-in-part of application No. 07/943,516, filed on Sep. 11, 1992, now abandoned.

(51) Int. Cl.[7] .................... C07H 21/02; C07H 21/04; C12Q 1/68

(52) U.S. Cl. .............. 536/23.1; 536/22.1; 536/24.3; 536/24.31; 536/25.3; 435/6

(58) Field of Search ................. 536/23.1, 25.3, 536/24.31, 24.3, 22.1; 435/6

(56) References Cited

U.S. PATENT DOCUMENTS

| | | | |
|---|---|---|---|
| 4,515,781 A | 5/1985 | Torrence et al. | 514/46 |
| 4,840,892 A | 6/1989 | Adams et al. | 435/5 |
| 4,849,513 A | 7/1989 | Smith et al. | 536/27 |
| 5,034,506 A | 7/1991 | Summerton et al. | 528/391 |
| 5,138,045 A | 8/1992 | Cook et al. | 536/27 |
| 5,543,507 A * | 8/1996 | Cook et al. | 536/23.1 |
| 5,834,231 A | 11/1998 | Stoddard et al. | 435/42 |

FOREIGN PATENT DOCUMENTS

| | | |
|---|---|---|
| EP | 398 231 | 11/1990 |
| WO | WO 91/10671 | 7/1991 |
| WO | WO 92/02531 | 2/1992 |

OTHER PUBLICATIONS

Bertrand et al, "Mechanism of cleavage of apurinic sites by 9–aminoellipticine", J. Biol. Chem. (1989) 264:14172–14178.*

Bayard, B. et al., "Activation of Ribonuclease L by (2'–5')(A)[4]–Poly(L–lysine) Conjugates in Intact Cells", Biochemistry 1986, 25, 3730–3736.

Behr, J., "DNA Strongly Binds to Micelles and Vesicles Containing Lipopolyamines or Lipointercalants", Tetrahedron Letters 1986, 27(48), 5861–5864.

Ceruzzi, M. and Draper, "The Intracellular and Extracellular Fate of Oligodeoxyribonucleotides in Tissue Culture Systems", Nucleosides & Nucleotides 1989, 8(5&6), 815–818.

Doetsch, P. and Cunningham, "The Enzymology of Apurinic–Apyrimidinic Endonucleases", Mutation Research 1990, 236, 173–201.

Fory, W. and McCormick, "Chemical Synthesis of Flavin Coenzymes", Methods in Enzymology 1971, vol. 18 Part B, 458–464.

Friedberg, E., "DNA Repair", pp. 153, W.H. Freeman & Company, New York, 1985.

Goodchild, J., "Conjugates of Oligonucleotides and Modified Oligonucleotides: A Review of Their Synthesis and Properties", Bioconjugate Chemistry 1990, 1(3), 165–187.

Groehke, K. and Leumann, "A Method for Preparing Oligodeoxynucleotides Containing an Apurinic Site", Helvetica Chimica Acta 1990, 73, 608–617.

Horn, T. et al., "Controlled Chemical Cleavage of Synthetic DNA at Specific Sites", Nucleosides & Nucleotides 1991, 10(1–3), 299–302.

Inoue, H. et al., "Synthesis and Hybridization Studies on Two Complementary Nona(2'–O–methyl)ribonucleotides", Nucleic Acids Res. 1987, (15(15), 6131–6148.

Iocono, J. et al., "Mild Acid Hydrolysis of 2–Pyrimidinone–Containing DNA Fragments Generates Apurinic/Apyrimidinic Sites", Tetrahedron Letters 1990, 31(2), 175–178.

Le Doan, T. et al., "Sequence–targeted Chemical Modifications of Nucleic Acids by Complementary Oligonucleotides Covalently Linked to Porphyrins", Nucleic Acids Res. 1987, 15(21), 8643–8659.

Lemaitre, M. et al., "Specific Antiviral Activity of Poly(L–lysine)–conjugated Oligodeoxyribonucleotide Sequence Complementary to Vesicular Virus N Protein mRNA Initiation Site", PNAS USA 1987, 84, 648–652.

Letsinger, R. et al., "Cholesteryl–conjugated Oligonucleotides: Synthesis, Properties, and Activity as Inhibitors of Replication of Human Immunodeficiency Virus in Cell Culture", PNAS USA 1989, 86, 6553–6556.

Lindahl, T. et al., "DNA N–Glycosidases. Properties of Uracil–DNA Glycosidase from Escherichia coli", The J. of Biol. Chem. 1977, 252(10), 3286–3294.

Loke, S.L. et al., "Delivery of c–myc Antisense Phosphorothioate Oligodeoxynucleotides to Hematopoietic Cells in Culture by Liposome Fusion: Specific Reduction in c–myc Protein Expression Correlates with Inhibition of Cell Growth and DNA Synthesis", Current Topics in Microb. and Immunol. 1988, 141, 282–289.

Iyer, R. et al., "Abasic Oligodeoxyribonucleoside Phosphorothioates: Synthesis and evaluation as Anti–HIV–1 Agents", Nucleic Acids Res. 1990, 18(10), 2855–2859.

Manoharan, M. et al., "Mechanism of UV Endonuclease V Cleavage of Abasic Sites in DNA Determined by ⁻C Labeling", J. of Am. Chem. Soc. 1988, 110, 2690–2691.

(List continued on next page.)

Primary Examiner—Jeffrey Fredman
(74) Attorney, Agent, or Firm—Woodcock Washburn LLP

(57) ABSTRACT

Novel amine compounds are provided by the present invention. Methods of preparing and using said novel amine compounds are also provided.

4 Claims, 3 Drawing Sheets

OTHER PUBLICATIONS

Marcus–Sekura, C. et al., "Comparative Inhibition of Chloramphenicol Acetyltransferase Gene Expression by Antisense Oligonucleotide Analogues Having Alkyl Phosphotriester, Methylphosphonate and Phosphorothioate Linkages", *Nucleic Acids Res.* 1987, 15(14), 5749–5763.

Miller, P.S. et al., "Biochemical and Biological Effects of Nonionic Nucleic Acid Methylphosphonates", *Biochemistry* 1981, 20, 1874–1880.

Miller, P.S. et al., "Effects of a Trinucleotide Ethyl Phosphotriester, G$^m$p(Et)G$^m$p(Et)U, on Mammalian Cells in Culture", *Biochemistry* 1977, 16(9).

Nielsen P. et al., "Sequence–Selective Recognition of DNA by Strand Displacement with a Thymine–Substituted Polyamide", *Science* 1991 254, 1497–1500.

Poec'h, D. et al., "Efficient Chemical Synthesis of Oligonucleotides Containing a True Abasic Site", *Tetrahedron Letters* 1991, 32(2), 207–210.

Robins, M. et al., "Nucleic Acid Related Compounds. 12. The Facile and High–Yield Stannous Chloride Catalyzed Monomethylation of the Cis–Glycol System of Nucleosides by Diazomethane", *J. Org. Chem.* 1974, 39(13), 1891–1899.

Robins, M. et al., "Nucleic Acid Related Compounds. 36. Synthesis of the 2'–O–methyl and 3'–O–methyl Ethers of Guanosine and 2–Aminoadenosine and Correlation of O'–methylnucleoside $^{13}$C nmr Spectral Shifts", *Can. J. Chem.* 1981, 59, 3360–3364.

Sakumi, K. and Sekiguchi, "Structures and Functions of DNA Glycosylases", *Mutation Res.* 1990, 236, 161–172.

Sawai, H. et al., "Synthesis and Biological Activities of β–Alanyltyrosine Derivative of 2',5'–Oligoadneylate, and Its Use in radiobinding Assay for 2',5'–Oligoadenylate", *J. Biochem.* 1987, 101, 339–346.

Sawai, H. et al., "Sensitive Radioimmuno Assay for 2'–5'–Oligoadenylates Using a Novel $^{125}$I–Labeled Derivative of 2',5'–Triadenylate 5'–Triphosphate", *J. Biochem.* 1985, 98, 999–1005.

Smith–Jones, P. et al., "Antibody Labeling with Copper–67 Using the Bifuncitonal Macrocycle 4'–[1,4,8, 11–Tetraazacyclotetradec–1–yl)methyl]benzoic Acid", *Bioconjugate Chem.* 1991, 2, 415–421.

Stevenson, M. and Iversen, "Inhibition of Human Immunodeficiency Virus Type 1–mediated Cytopathic Effects by Poly(L–lysine)–conjugated Synthetic Antisense Oligodeuxyribonucleotides", *J. gen. Virol.* 1989, 70, 2673–2682.

Studer, M. and Kaden, "220. Metal Complexes with Macrocyclic Ligands. Part XXV, One–Step Synthesis of Mono–N–Substituted Azamacrocycles with a Carboxylic Group in the Side–Chain and their Complexes with $Cu^{2+}$ and $Ni^{2+}$", *Helvetica Chim. Acta* 1986, 69, 2081–2086.

Suh, J. et al., "Macrocyclic Metal Complexes Built on Polyethylenimine", *J. Am. Chem. Soc.* 1991, 113, 4198–4202.

Tagaki, W. and Yamamoto, "Polyamino–β–Cyclodextrin as a Model of Aldolase", *Tetrahedron Letters* 1991, 32(9), 1207–1208.

Uhlmann, E. and Peyman, "Antisense Oligonucleotides: A New Therapeutic Principle", *Chemical Reviews* 1990, 90(4), 543–584.

Vasseur, J. et al., "Derivatization of Oligonucleotides Through Ascite Site Formation", *Nucleosides & Nucleotides* 1991, 10(1–3), 107–117.

Wilde, J. andl Bolton, "Characterization of the Equilibrating Form of the Aldehydic Abasic Site in Duplex DNA by $^{17}$O NMR", *J. Am. Chem. Soc.* 1989, 111, 1894–1896.

Wilson, D., "Cellular Transport Mechanisms", *Ann. Rev. Biochem.* 1978, 47, 933–965.

Wu, G. and Wu, "Evidence for Targeted Gene Delivery to Hep G2 Hepatoma Cells in Vitro", *Biochemistry* 1988, 27, 887–892.

Yoshinari, K. et al., "Oligoamines as Simple and Efficient Catalysts for RNA Hydrolysis", *J. Am. Chem. Soc.* 1991, 113, 5899–5901.

Zon, G., "Oligonucleotide Analogues as Potential Chemotherapeutic Agents", *Pharmaceutical Res.* 1988, 5(9), 539–549.

Zon, G., in "Oligodeoxynucleotides: Antisense Inhibitors of Gene Expression", pp. 234–247, Cohen, J.S., ed., CRC Press, Boca Raton, FL 1989.

Benimetskaya, et al., "Site specific laser modification(cleavage) of oligodeoxynucleotides", *Biopolymers,* 1989, 28, 1129–1147.

Nakagami, et al., "Preparation of enzyme–conjugated DNA probe and application to the universal probe system," *Anal. Biochem.,* 1991, 198, 75–79.

Sharma, et al., "Preparation and biological activity of some aminoacyl and peptidyl derivatives of 2'–amino–2'deoxyuridine," *J. Med. Chem.,* 1975, 18(9), 955–957.

Singleton, et al., Dictionary of Microbiology and Molecular Biology, 2$^{nd}$ Ed., John Wiley & Sons, NY, p. 691.

Taiji, et al., "Slow transacylation of peptidyladenosine allows analysis of the 2'/3' insomer specificity of peptidyl transferase," *Biochemistry,* 1985, 24, 5776–5780.

\* cited by examiner

3'- OLIGO POLYAMINE CONJUGATION

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

TGGGAGCCAT AGCGAGGCUC G                                              21

(2) INFORMATION FOR SEQ ID NO: 2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 19
        (D) OTHER INFORMATION: /note= "abasic, aldehydic
            species"

(xi) SEQUENCE DESCRIPTION: SEQ ID NO: 2:

TGGGAGCCAT AGCGAGGCN                                                 19

(2) INFORMATION FOR SEQ ID NO: 3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 6
        (D) OTHER INFORMATION: /note= "2'deoxyuridine
            residue"

(xi) SEQUENCE DESCRIPTION: SEQ ID NO: 3:

CGCAGUCAGC C                                                         11

(2) INFORMATION FOR SEQ ID NO: 4:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 6
        (D) OTHER INFORMATION: /note= "abasic residue"

(xi) SEQUENCE DESCRIPTION: SEQ ID NO: 4:

CGCAGNCAGC C                                                                                       11

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 9
        (D) OTHER INFORMATION: /note= "2'deoxyuridine
             residue"

(ix) FEATURE:
        (A) NAME/KEY: misc_ feature
        (B) LOCATION: 18
        (D) OTHER INFORMATION: /note= "2'deoxyuridine
             residue"

(xi) SEQUENCE DESCRIPTION: SEQ ID NO: 5:

GACAGAGGUA GGAGAAGUGA                                                                              20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 9
        (D) OTHER INFORMATION: /note= "abasic residue"

(ix) FEATURE:
        (A) NAME/KEY: misc_ feature
        (B) LOCATION: 18
        (D) OTHER INFORMATION: /note= "abasic residue"

(xi) SEQUENCE DESCRIPTION: SEQ ID NO: 6:

GACAGAGGNA GGAGAAGNGA                                                                              20

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

TGGGAGCCAT AGCGAGGC                                                                                18

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single

```
        (D) TOPOLOGY: linear (ii) MOLECULE TYPE: DNA (genomic)

(ix) FEATURE:
        (A) NAME/KEY: misc_ feature
        (B) LOCATION: 9
        (D) OTHER INFORMATION: /note=
            "2'-O -aminopentoxy-2'-deoxyadenosine"

(xi) SEQUENCE DESCRIPTION: SEQ ID NO: 8:

CTGTCTCCAT CCTCTTCACT                                               20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CTGTCTCCAT CCTCTTCACT                                               20

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 5
        (D) OTHER INFORMATION: /note= "2'deoxyuridine
            residue"

(ix) FEATURE:
        (A) NAME/KEY: misc_ feature
        (B) LOCATION: 7
        (D) OTHER INFORMATION: /note= "2'deoxyuridine
            residue"

(ix) FEATURE:
        (A) NAME/KEY: misc_ feature
        (B) LOCATION: 21
        (D) OTHER INFORMATION: /note= "2'-aminopropoxy
            cytosine"

(xi) SEQUENCE DESCRIPTION: SEQ ID NO: 10:

GGCGUCUCCA GGCGAUCUGA C                                             21

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 20
        (D) OTHER INFORMATION: /note= "2'-aminopropoxy
            cytosine"
```

(xi) SEQUENCE DESCRIPTION: SEQ ID NO: 11:

TCTGAGTAGC AGAGGAGCTC                                                        20

(2) INFORMATION FOR SEQ ID NO: 12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_ feature
            (B) LOCATION: 4
            (D) OTHER INFORMATION: /note= "2'deoxyuridine
                residue"

(ix) FEATURE:
            (A) NAME/KEY: misc_ feature
            (B) LOCATION: 9
            (D) OTHER INFORMATION: /note= "2'deoxyuridine
                residue"

(ix) FEATURE:
            (A) NAME/KEY: misc_ feature
            (B) LOCATION: 11
            (D) OTHER INFORMATION: /note= "2'deoxyuridine
                residue"

(ix) FEATURE:
            (A) NAME/KEY: misc_ feature
            (B) LOCATION: 20
            (D) OTHER INFORMATION: /note= "2'deoxyuridine
                residue"

(ix) FEATURE:
            (A) NAME/KEY: misc_ feature
            (B) LOCATION: 21
            (D) OTHER INFORMATION: /note= "2'-aminopropoxy
                cytosine"

(xi) SEQUENCE DESCRIPTION: SEQ ID NO: 12:

GGAUGGCGUC UCCAGGCGAU C                                                      21

(2) INFORMATION FOR SEQ ID NO: 13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_ feature
            (B) LOCATION: 4
            (D) OTHER INFORMATION: /note= "2'deoxyuridine
                residue"

(ix) FEATURE:
            (A) NAME/KEY: misc_ feature
            (B) LOCATION: 9
            (D) OTHER INFORMATION: /note= "2'deoxyuridine
                residue"

(ix) FEATURE:
            (A) NAME/KEY: misc_ feature
            (B) LOCATION: 11
            (D) OTHER INFORMATION: /note= "2'deoxyuridine
                residue"

(ix) FEATURE:

```
        (A) NAME/KEY: misc_ feature
        (B) LOCATION: 20
        (D) OTHER INFORMATION: /note= "2'deoxyuridine
             residue"

(xi) SEQUENCE DESCRIPTION: SEQ ID NO: 13:

GGAUGGCGUC UCCAGGCGAU C                                             21

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 18
        (D) OTHER INFORMATION: /note= "2'deoxyuridine
             residue"

(xi) SEQUENCE DESCRIPTION: SEQ ID NO: 14:

TGGGAGCCAT AGCGAGGUCT                                               20

(2) INFORMATION FOR SEQ ID NO: 15:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 3
        (D) OTHER INFORMATION: /note= "2'deoxyuridine
             residue"

(xi) SEQUENCE DESCRIPTION: SEQ ID NO: 15:

GAUCT                                                                5

(2) INFORMATION FOR SEQ ID NO: 16:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_ feature
        (B) LOCATION: 3
        (D) OTHER INFORMATION: /note= "abasic residue"

(xi) SEQUENCE DESCRIPTION: SEQ ID NO: 16:

GANCT                                                                5
```

OLIGONUCLEOTIDE AND NUCLEOTIDE AMINE ANALOGS, METHODS OF SYNTHESIS AND USE

This patent application is a division of U.S. patent application Ser. No. 08/397,277, filed Mar. 9, 1995, now U.S. Pat. No. 6,235,886, which is a continuation-in-part of patent application Ser. No. 07/943,516, filed on Sep. 11, 1992, now abandoned and is a 371 of PCT 93/08367 filed Sep. 3, 1993. The foregoing patents and patent applications are assigned to the same assignee as this patent application and are incorporated herein by reference.

FIELD OF THE INVENTION

This invention relates to novel amine-containing compounds useful for therapeutics and methods of making and using the same.

BACKGROUND OF THE INVENTION

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. These interactions involved the binding of complementary "antisense" oligonucleotides or their analogs to the trans-cellular RNA in a sequence specific fashion such as by Watson-Crick base pairing interactions.

The pharmacological activity of antisense compounds, as well as other therapeutics, depends on a number of factors that influence the effective concentration of these agents at specific intracellular targets. One important factor is the ability of antisense compounds to traverse the plasma membrane of specific cells involved in the disease process.

Cellular membranes consist of lipid protein bilayers that are freely permeable to small, nonionic, lipophilic compounds and inherently impermeable to most natural metabolites and therapeutic agents. Wilson, *Ann. Rev. Biochem.* 1978, 47, 933. The biological and antiviral effects of natural and modified oligonucleotides in cultured mammalian cells have been well documented, so it appears that these agents can penetrate membranes to reach their intracellular targets. Uptake of antisense compounds into a variety of mammalian cells, including HL-60, Syrian Hamster fibroblast, U937, L929, CV-1, and ATH8 cells has been studied using natural oligonucleotides and nuclease resistant analogs, such as alkyl triesters, Miller, et al., *Biochemistry* 1977, 16, 1988; methylphosphonates, Marcus-Sekura, et al., *Nuc. Acids Res.* 1987, 15, 5749 and Miller, et al., *Biochemistry* 1981, 20, 1874; and phosphorothioates, Ceruzzi, et al., *Nucleosides & Nucleotides* 1989, 8, 815; Miller, et al., *Biochemistry* 1987, 16, 1988; and Loke, et al., *Curr. Top. Microbiol. Immunol.* 1988, 141, 282.

Enhanced cellular uptake has previously been achieved by attachment of functional groups to the 3' and 5' end of oligonucleotides to enhance cellular uptake in specific cell types. Previous studies have shown that plasmid DNA completed with an (asialo)glycoprotein-poly(L-lysine) conjugate, could be targeted to hepatocytes, which contain unique cell surface receptors for galactose-terminal (asialo) glycoproteins. Wu, et al., *Biochemistry* 1988, 27, 887. Other groups have synthesized oligodeoxyribonucleotides that have a 5'-attached alkylating agent and a 3' attached cholesterol moiety and determined that these modified oligonucleotides were taken up into cells more efficiently than control compounds without the steroid moiety. Zon, G. in *Oligodeoxynucleotides: Antisense Inhibitors of Gene Expression* 234–247, ed. J. S. Cohen (CRC Press, Boca Raton Fla., 1989). Letsinger, et al., *Proc. Natl. Acad. Sci. U.S.A.* 1989, 86, 653, have also synthesized cholesteryl-conjugated phosphorothioates whose anti-HIV activity is significantly greater than natural oligonucleotides with the same sequence. Additional modifications include conjugation of oligonucleotides to poly(L-lysine) alone. Stevenson, et al., *J. Gen. Virol* 1989, 70, 2673 and Lemaitre, et al., *Proc. Natl. Acad. Sci. U.S.A.* 1987, 84, 648. This modification enhanced the antiviral activity of the compound studied presumably due to increased cellular uptake imparted by the polycationic poly(L-lysine).

The conjugation of polyamines to oligonucleotides have been found to enhance cellular uptake of oligonucleotides, increased lipophilicity, cause greater cellular retention and increased distribution of the compound. Vasseur, *Nucleosides and Nucleotides* 1991, 10, 107 prepared abasic sites at different sites of oligothymidylates by acid hydrolysis. Thereafter the abasic sites were functionalized with functionalities such as 3-amino carbazole, 9-amino elipticine and psoralen. Vasseur, et al., also refer to unpublished results in which the functionalities spermidine and proflavin were employed. The abasic site was generated by one of the following three methods: (i) selective depurination by acid treatment in a pyrimidine-rich oligonucleotide having one purine in a chosen site, (ii) incorporating 2',3'-dideoxynebularine at the 5'-end with the nebularine phosphoramidite at the last step of the oligonucleotide synthesis, and subsequent acid treatment (30 mM HCl at 37° C.) to create an abasic site at 5' end (in this case the open-chain structure is CHO—(CH$_2$)$_2$—CHOH—CH$_2$O— at the 5' end and the conjugate from the amine RNH$_2$ is RNH—(CH$_2$)$_3$—CHOH—CH$_2$—O-Oligo), and (iii) incorporating a protected abasic 2'-deoxy-D-ribofuranose nucleotide synthon that has a photo-labile O-nitrobenzyl group as the anomeric hydroxyl-protecting group in oligonucleotide synthesis and removing it prior to conjugation.

Groebke and Leumann used a silyl-protecting group at the anomeric center to generate the abasic site. 2'-Deoxy-5-O-dimethoxytrityl-D-ribofluranose was silylated at the 1-O-position using TBDMSCl and the silyl group was removed later by hydrolysis at pH 2.0 to yield the abasic site. Unfortunately, fluoride-ion-mediated deprotection of the silyl group caused a β-elimination and DNA degradation.

McLaughlin's group has utilized 1-(β--D-2-deoxyribosyl)-2-pyrimidone-based phosphoramidite to generate abasic sites at pH3.0. The N-glycosyl cleavage occured, however, slower in oligonucleotides than in parent nucleosides; nearly 60 hours of acid treatment was necessary to generate 90% abasic site formation. However, conjugation chemistry via enzymatically generated abasic sites are unknown in the literature.

Le Doan, et al., *Nucleic Acids Research* 1987, 15, 8643 teaches oligothymidylates covalently linked to porphyrins at their 3' end via one of the linkers —O—CH$_2$—CO—NH—(CH$_2$)$_2$—NH or PO$_4$—(CH$_2$)$_6$—NH—. Le Doan, et al., also used the linker PO$_4$—(CH$_2$)$_6$—NH— to link porphyrins to the 5' end of oligothymidylates. Another group, Summerton, et al., U.S. Pat. No. 5,034,506 issued Jul. 23, 1991 teaches morpholino subunits, linked together by uncharged, achiral linkages such as amides. As described in PCT/US91/04086 filed Jun. 10, 1991, polyamines have also been linked at the 5' end of an oligonucleotide at the 5' site of the sugar moiety of the terminal nucleoside and at the 2-position carbon of the heterocyclic base of 2'-deoxyadenosine, 2'-deoxyguanosines and other purines and purine analogs by known procedures as described in PCT/US/91/00243 filed Jan. 11, 1991.

Novel amines and methods of preparing the same are greatly needed in order to enhance cellular uptake of oligonucleotides, increase lipophilicity, cause greater cellular retention and increase distribution of the compound within the cell. The present invention fulfills this need.

OBJECTS OF THE INVENTION

It is one object of the present invention to provide novel amine-containing compounds useful in therapeutics.

It is a further object of the present invention to provide methods of producing said novel compounds.

It is another object of the present invention to provide methods of modulating the production of a protein by an organism.

It is still a further object of the present invention to provide methods of treating a mammal suffering from a disease characterized by the undesired production of a protein.

It is yet a further object of the present invention to provide methods of diagnosing the presence of an RNA in a biological sample.

These and other objects will become apparent from the following description and accompanying claims.

SUMMARY OF THE INVENTION

The present invention provides compounds which may have enhanced efficacy as an antisense-based therapy. Compounds of the present invention can have enhanced cellular uptake, increased lipophilicity, cause greater cellular retention and demonstrate increased distribution. Furthermore the present invention provides simple methods for synthesis of these novel compounds.

In accordance with some embodiments of the present invention, compounds having the structure:

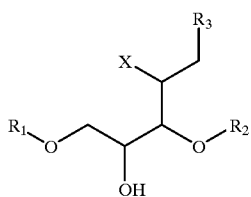

I wherein $R_1$ and $R_2$ are independently H, a nucleotide, oligonucleotide, or an amine-containing species, and at least one of $R_1$ and $R_2$ is a purine containing oligonucleotide, $R_3$ is a linear or cyclic amine-containing species, and X is H, O—$R_{11}$, S—$R_{11}$, F, Cl, Br, CN, $CF_3$, $OCF_3$, OCN, $SOCH_3$, $SO_2CH_3$, $ONO_2$, $N_3$, $HN_2$, heterocylcoalkyl, heterocycloalkaryl, aminoalkylamino, polyalkylamino, substituted silyl, a reporter molecule, an RNA cleaving group, a group for improving the pharmacokinetic properties of an oligonucleotide, or a group for improving the pharmacodynamic properties of an oligonucleotide wherein $R_{11}$ is H, $C_1$ to $C_{10}$ straight or branched chain lower alkyl or substituted lower alkyl, $C_2$ to $C_{10}$ straight or branched chain lower alkenyl or substituted lower alkenyl, $C_3$ to $C_{10}$ straight or branched chain lower alkynyl or substituted lower alkynyl, a $^{14}C$ containing lower alkyl, lower alkenyl or lower alkynyl, $C_7$ to $C_{14}$ substituted or unsubstituted alkyaryl or aralkyl, a $^{14}C$ containing $C_7$ to $C_{14}$ alkaryl or aralkyl, alicyclic, heterocyclic, a reporter molecule, a RNA cleaving group, a group for improving the pharmacokinetic properties of an oligonucleotide or a group for improving the pharmacodynamic properties of an oligonucleotide, are provided.

In accordance with still other embodiments of the present invention, compounds having the structure:

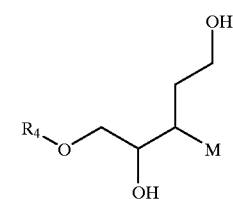

II wherein $R_4$ is an oligonucleotide and M is a pendent group having an amine-containing species attached thereto are provided.

Methods of preparing such compounds utilizing enzymatic reagents are also provided in some aspects of the invention. Thus compounds of Formula I may be prepared by methods comprising the steps of providing a synthon having the structure:

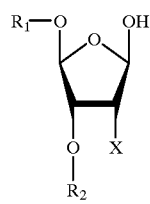

wherein $R_1$ and $R_2$ are independently H, a nucleotide, oligonucleotide or amine-containing species, and at least one of $R_1$ and $R_2$ is a purine containing oligonucleotide, and X is H, O—$R_{11}$, S—$R_{11}$, F, Cl, Br, CN, $CF_3$, $OCF_3$, OCN, $SOCH_3$, $SO_2CH_3$, $ONO_2$, $N_3$, $HN_2$, heterocylcoalkyl, heterocycloalkaryl, aminoalkylamino, polyalkylamino, substituted silyl, a reporter molecule, an RNA cleaving group, a group for improving the pharmacokinetic properties of an oligonucleotide, or a group for improving the pharmacodynamic properties of an oligonucleotide wherein $R_{11}$ is H, $C_1$ to $C_{10}$ straight or branched chain lower alkyl or substituted lower alkyl, $C_2$ to $C_{10}$ straight or branched chain lower alkenyl or substituted lower alkenyl, $C_3$ to $C_{10}$ straight or branched chain lower alkynyl or substituted lower alkynyl, a $^{14}C$ containing lower alkyl, lower alkenyl or lower alkynyl, $C_7$ to $C_{14}$ substituted or unsubstituted alkyaryl or aralkyl, a $^{14}C$ containing $C_7$ to $C_{14}$ alkaryl or aralkyl, alicyclic, heterocyclic, a reporter molecule, a RNA cleaving group, a group for improving the pharmacokinetic properties of an oligonucleotide or a group for improving the pharmacodynamic properties of an oligonucleotide. Thereafter the synthon is reacted with $R_3$, wherein $R_3$ is a linear or cyclic amine-containing species, under reducing conditions to yield the final product.

Compounds of Formula II may also be prepared enzymatically by providing a starting material having the structure:

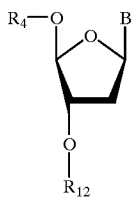

wherein $R_4$ is an oligonucleotide, $R_{12}$ is an oligonucleotide and B is urea or a heterocyclic base having a corresponding glycosylase and reacting the starting material with an endonuclease to generate a conjugated α,β-unsaturated system in the sugar residue of the 3' terminal nucleotide. Thereafter the compound having a conjugated α,β-unsaturated system is reacted with a pendent group containing a nucleophile functionality thereon. Following addition of the pendent group the double bond of the α,β system is reduced with a reducing agent. An amine-containing species may then be attached to the pendent group via an alkylation reaction. Alternatively, an amine-containing species may be attached to a pendent group which is a bifunctional linker.

In accordance with still other embodiments of the present invention compounds having the structure:

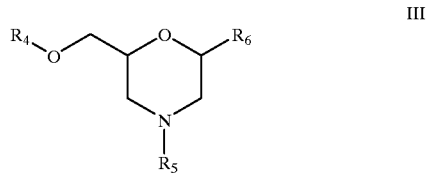

III wherein $R_4$ is an oligonucleotide, $R_5$ is a linear or cyclic amine-containing species containing at least one non-amide nitrogen atom, and $R_6$ is H, a purine heterocycle or a pyrimidine heterocycle, are provided. Methods of preparing compounds of Formula III are also provided in some aspects of the present invention comprising the steps of reacting an oligonucleotide having a 3' ribofuranosyl sugar with an oxidizing agent to produce an activated dialdehyde-terminated oligonucleotide and reacting said activated oligonucleotide with a linear or cyclic amine-containing species under reducing conditions to yield said compound.

In accordance with other aspects of the invention compounds having the structure:

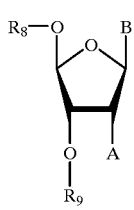

IV wherein B is a purine or pyrimidine heterocyclic base, $R_8$ and $R_9$ are independently H, $PO_2^-$, a nucleotide, an oligonucleotide or an amine-containing species, and at least one of $R_8$ and $R_9$ is a purine containing oligonucleotide, and at least one of $R_8$, $R_9$ and A is a species comprising the formula $L_1$—$L_2$-polyamine wherein $L_1$ is an amino linker and $L_2$ is a heterobifunctional linker; and wherein if $R_8$ is not a purine containing ligonucleotide or polyamine species, then $R_8$ is a nucleotide or $PO_2^-$; if $R_9$ is not a purine containing oligo- nucleotide or polyamine species, then $R_9$ is H or a nucleotide; and if A is not a polyamine species then A is H or OH are provided.

Therapeutic and diagnostic methods are also encompassed by the present invention. Methods of modulating the production of protein by an organism comprising contacting an organism with a compound having the structure of Formula I, formula II, Formula III or Formula IV are encompassed by some embodiments of the present invention. In other aspects of the invention, methods of treating an animal having a disease characterized by undesired production of protein comprising contacting an animal with a compound having the structure of Formula I, Formula II, Formula III, or Formula IV in a pharmaceutically acceptable carrier are provided. Still other methods of the present invention provide methods for detecting the presence or absence of an RNA in a biological sample suspected of containing said RNA are provided comprising contacting a sample with a compound having the structure of Formula I, Formula II, Formula III or Formula IV wherein the compound is specifically hybridizable with the RNA and detecting the presence or absence of hybridization of the compound to the sample wherein hybridization is indicative of the presence of RNA in the sample.

DETAILED DESCRIPTION OF PREFERRED EMBODIMENTS

Figure 1:
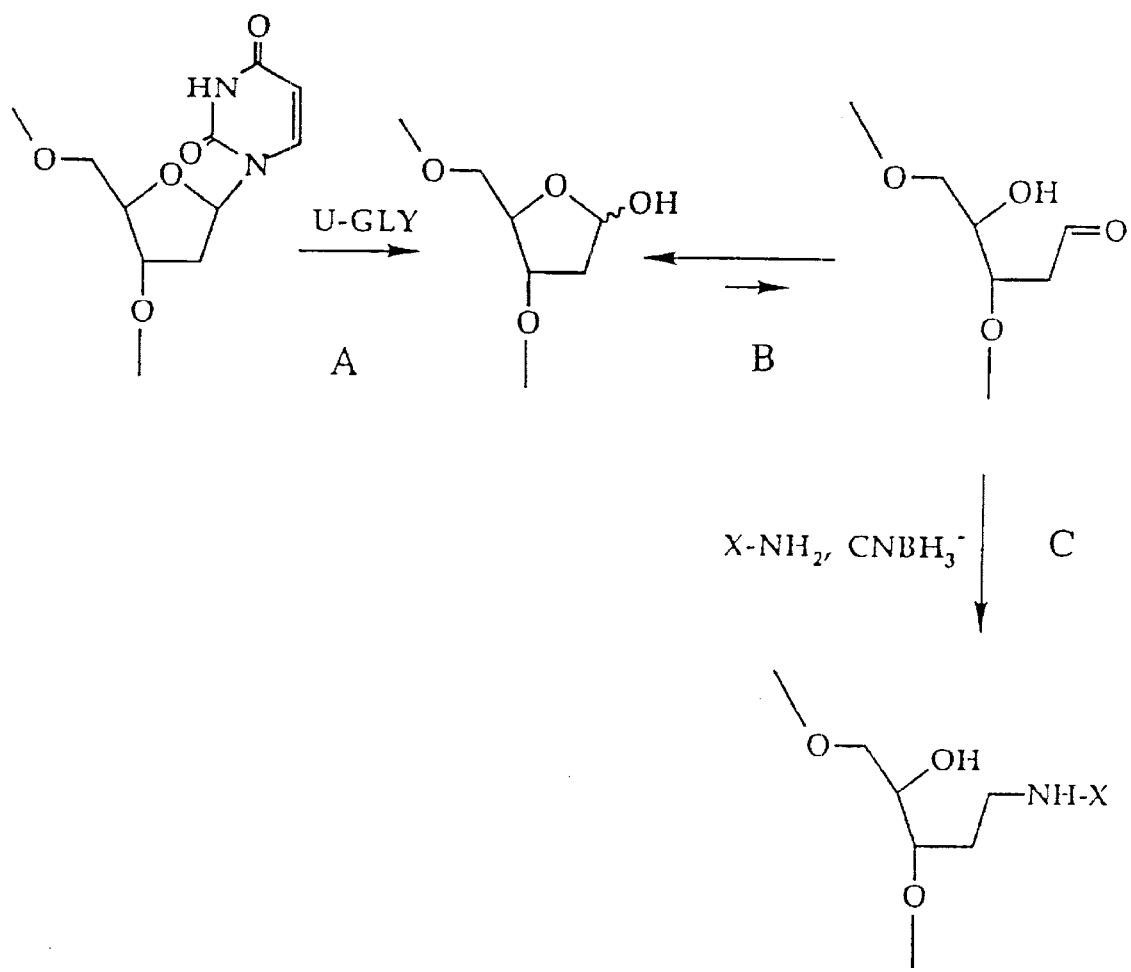
FIG. 1 is a schematic representation of one preferred syntheses of compounds of Formula I.

The present invention provides novel amine compounds useful for antisense therapy. In one embodiment of the present invention compounds having the structure:

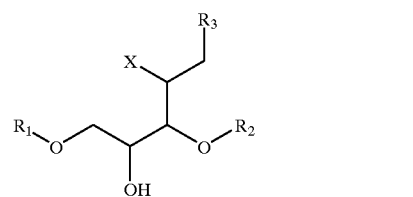

I wherein $R_1$ and $R_2$ are independently H, a nucleotide, an oligonucleotide, or an amine-containing species, and at least one of $R_1$ and $R_2$ is a purine containing oligonucleotide, $R_3$ is a linear or cyclic amine-containing species, and X is H, O—$R_{11}$, S—$R_{11}$, F, Cl, Br, CN, $CF_3$, $OCF_3$, OCN, $SOCH_3$, $SO_2CH_3$, $ONO_2$, $N_3$, $HN_2$, heterocylcoalkyl, heterocycloalkaryl, aminoalkylamino, polyalkylamino, substituted silyl, a reporter molecule, an RNA cleaving group, a group for improving the pharmacokinetic properties of an oligonucleotide, or a group for improving the pharmacodynamic properties of an oligonucleotide wherein $R_{11}$ is H, $C_1$ to $C_{10}$ straight or branched chain lower alkyl or substituted lower alkyl, $C_2$ to $C_{10}$ straight or branched chain lower alkenyl or substituted lower alkenyl, $C_3$ to $C_{10}$ straight or branched chain lower alkynyl or substituted lower alkynyl, a $^{14}C$ containing lower alkyl, lower alkenyl or lower alkynyl, $C_7$ to $C_{14}$ substituted or unsubstituted alkyaryl or aralkyl, a $^{14}$C containing $C_7$ to $C_{14}$ alkaryl or aralkyl, alicyclic, heterocyclic, a reporter molecule, a RNA cleaving group, a group for improving the pharmacokinetic properties of an oligonucleotide or a group for improving the pharmacodynamic properties of an oligonucleotide, are provided. In some embodiments of the present invention both $R_1$ and $R_2$ are oligonucleotides, at least one of which includes at least one purine nucleotide.

In the context of this invention, the term "oligonucleotide" refers to a polynucleotide formed from naturally occurring bases, such as purine and pyrimidine heterocycles, and furanosyl groups joined by native phosphodiester bonds. This term effectively refers to naturally occurring species or synthetic species formed from naturally occurring subunits or their close homologs. The term "oligonucleotide" may also refer to moieties which have portions similar to naturally occurring oligonucleotides but which have non-naturally occurring portions. Thus, oligonucleotides may have altered sugar moieties or inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the viral RNA is located. It is preferred that such substitutions comprise phosphorothioate bonds, phosphotriesters, methyl phosphonate bonds, short chain alkyl or cycloalkyl structures or short chain heteroatomic or heterocyclic structures. Most preferred are $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ structures where phosphodiester is O—P—O—$CH_2$). Also preferred are morpholino structures. Summerton, et al., U.S. Pat. No. 5,034,506 issued Jul. 23, 1991. In other preferred embodiments, such as the protein-nucleic acid (PNA) backbone, the phosphodiester backbone of the oligonucleotide may be replace with a polyamide backbone, the bases being bound directly or indirectly to the aza nitrogen atoms of the polyamide backbone. see, e.g., Nielsen, et al., *Science* 1991, 254 1497 and WO 92/20702, published Nov. 26, 1992. In accordance with other preferred embodiments, the phosphodiester bonds are substituted with other structures which are, at once, substantially non-ionic and non-chiral, or with structures which are chiral and enantiomerically specific. Still other linkages include the those disclosed in U.S. patent applications Ser. No. 566,836, filed Aug. 13, 1990, entitled Novel Nucleoside Analogs; Ser. No. 703,619, filed May 21, 1991, entitled Backbone Modified Oligonucleotide Analogs; Ser. No. 903,160, filed Jun. 24, 1992, entitled Heteroatomic oligonucleoside Linkages; Ser. No. PCT/US92/04294, filed May 21, 1992, entitled Backbone Modified Oligonucleotides; and Ser. No. PCT/US92/04305, all assigned to the assignee of this invention. Persons of ordinary skill in the art will be able to select other linkages for use in practice of the invention.

Oligonucleotides may also include species which include at least some modified base forms. Thus, purines and pyrimidines other than those normally found in nature may be so employed. For example, deaza or aza purines and pyrimidines may be used in place of naturally purine or pyrimidine bases and pyrimidine bases having substituent groups at the 5- or 6-positions; purine bases having altered or replacement substituent groups at the 2-, 6- or 8-positions are also provided in some aspects of the present invention. Similarly, modifications on the furanosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n NH_2$, $O(CH_2)_n CH_3$ where n is from 1 to about 10; $C_1$ to $C_{10}$ lower alkyl, substituted lower alkyl, alkaryl or aralkyl; Cl, Br, CN, $CF_3$, $OCF_3$, O—, S—, or N-alkyl; O—, S—, or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Exemplary modifications are disclosed in U.S. patent applications: Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides; Ser. No. 558,806, filed Jul. 27, 1991, entitled Nuclease Resistant Pyrimidine Modified Oligonucleotides That Detect And Modulate Gene Expression; and Ser. No. PCT/US91/00243, filed Jan. 11, 1991, entitled Compositions and Methods For Detecting And Modulating RNA Activity; Ser. No. 777,670, filed Oct. 15, 1991, entitled Oligonucleotides Having Chiral Phosphorus Linkages; Ser. No. 814,961, filed Dec. 24, 1991, entitled Gapped 2' Modified Phosphorothioate oligonucleotides; Ser. No. 808,201, filed Dec. 13, 1991, entitled Cyclobutyl Oligonucleotide Analogs; and Ser. No. 782,374, filed 782,374, entitled Derivatized Oligonucleotides Having Improved Uptake & Other Properties, all assigned to the assignee of this invention. The disclosures of all of the above noted patent applications are incorporated herein by reference. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide. Thus, purine containing oligonucleotide are oligonucleotides comprising at least one purine base or analog thereof. In other embodiments of the present invention compounds of the present invention may be "subunits" of a species comprising two or more compounds of the present invention which together form a single oligonucleotide.

Oligonucleotides of the present invention may be naturally occurring or synthetically produced and may range in length from about 8 to about 50 nucleotides. In more preferred embodiments of the present invention said oligonucleotides may be from 8 to 40 nucleotides in length. Most preferably, oligonucleotides of the present invention may be from 12 to about 20 nucleotides in length.

Amine-containing species according to the invention are aromatic species containing a single nitrogen atom or non-aromatic species containing one or more nitrogen atoms (i.e., polyamine species). Amine-containing species can be linear (including straight-chain and branched) or cyclic. cyclic amine-containing species can be aromatic or non-aromatic. Representative amine-containing species include amino acids, polypeptides, hydrazide salts of organic acids, including one or more of reporter groups, alkylating agents, intercalating agents, cell receptor binding molecules, steroids, peptides, crown amines, porphyrins, cross-linking agents, peptide nucleic acids (PNA) and PEG (polyethylene glycol containing)-amines attached to at least one of the nitrogen atoms of said amine-containing species.

Polyamine species according to the invention are those that contain a plurality of nitrogen atoms. Polyamines include primary amines, hydrazines, semicarbazines, thiosemicarbazines and similar nitrogenous species. Such species can be symmetrical species such as polyamine-containing polymers or they can be unsymmetrical wherein the amine functionalities of the polyamine are separated in space by different moieties. In addition to carbon atoms other atomic species such as nitrogen and sulfur may also be incorporated into the polyamine species. In some preferred embodiments of the invention, at least one nitrogen atom of the polyamine has a free electron pair.

Preferred as polyamine species are species that range in length from about 3 to about 20 units. More preferably species having at least one nitrogen atom have the general formula $H_2N[(CH_2)_nNH]_m$— wherein n is an integer between 2 and 8 and m is an integer between 1 and 10. These species can be linear or cyclic. Cyclic amines would include crown amines ("cyclams") and mixed crown amines/crown ethers.

Other suitable amine-containing species according to the invention include $C_1-C_{20}$ straight chain alkylamine, $C_1-C_{20}$ straight chain substituted alkylamine, $C_2-C_{50}$ branched chain alkylamine, $C_2-C_5O$ branched chain substituted alkylamine, $C_3-C_{50}$ cyclic alkylamine, $C_3-C_{50}$ cyclic substituted alkylamine, $C_2-C_{20}$ straight chain alkenylamine, $C_2-C_{20}$ straight chain substituted alkenylamine, $C_3-C_{50}$ branched chain alkenylamine, $C_3-C_{50}$ branched chain substituted alkenylamine, $C_3-C_{50}$ cyclic alkenylamine, $C_3-C_{50}$ cyclic substituted alkenylamine, $C_2-C_{20}$ straight chain alkynylamine, $C_2-C_{20}$ straight chain substituted alkynylamine, $C_3-C_{50}$ branched chain alkynylamine, $C_3-C_{50}$ branched chain substituted alkynylamine, $C_3-C_{50}$ cyclic alkynylamine, $C_3-C_{50}$ cyclic substituted alkynylamine, $c_1-C_{20}$ straight chain alkylhydrazine, $C_1-C_{50}$ straight chain substituted alkylhydrazine, $C_2-C_{50}$ branched chain alkylhydrazine, $C_2-C_{50}$ branched chain substituted alkylhydrazine, $_3-C_{50}$ cyclic hydrazoalkane, $C_3-C_{50}$ cyclic substituted hydrazoalkane, $C_2-C_{20}$ straight chain alkenylhydrazine, $C_2-C_{20}$ straight chain substituted alkenylhydrazine, $C_3-C_{50}$ branched chain alkenylhydrazine, $C_3-C_{50}$ branched chain substituted alkenylhydrazine, $C_3-C_{50}$ cyclic hydrazoalkene, $C_3-C_{50}$ cyclic substituted hydrazoalkene, $C_2-C_{20}$ straight chain alkynylhydrazine, $C_2-C_{20}$ straight chain substituted alkynylhydrazine, $C_3-C_{50}$ branched chain alkynylhydrazine, $C_3-C_{50}$ branched chain substituted alkynylhydrazine, $C_3-C_{50}$ cyclic hydrazoalkyne, $C_3-C_{50}$ cyclic substituted hydrazoalkyne, $C_1-C_{20}$ straight chain alkylhydroxyamine, $C_1-C_{20}$ straight chain substituted alkylhydroxyamine, $C_2-C_{50}$ branched chain alkylhydroxyamine, $C_2-C_{50}$ branched chain substituted alkylhydroxyamine, $C_3-C_{50}$ cyclic oxyalkylamine, $C_3-C_{50}$ cyclic substituted oxyalkylamine, $C_2-C_{20}$ straight chain alkenylhydroxyamine, $C_2-C_{20}$ straight chain substituted alkenylhydroxyamine, $C_3-C_{50}$ branched chain alkenylhydroxyamine, $C_3-C_{50}$ branched chain substituted alkenylhydroxyamine, $C_3-C_{50}$ cyclic oxyalkenylamine, $C_3-C_{50}$ cyclic substituted oxyalkenylamine, $C_2-C_{20}$ straight chain alkynylhydroxyamine, $C_2-C_{20}$ straight chain substituted alkynylhydroxyamine, $C_3-C_{50}$ branched chain alkynylhydroxyamine, $C_3-C_{50}$ branched chain substituted alkynylhydroxyamine, $C_3-C_{50}$ cyclic oxyalkynylamine, $C_3-C_{50}$ cyclic substituted oxyalkynylamine, $C_1-C_{20}$ straight chain alkylsemicarbazide, $C_1-C_{20}$ straight chain substituted alkylsemicarbazide, $C_2-C_{50}$ branched chain alkylsemicarbazide, $C_2-C_{50}$ branched chain substituted alkylsemicarbazide, $C_3-C_{50}$ cyclic alkylsemicarbazide, $C_3-C_{50}$ cyclic substituted alkylsemicarbazide, $C_2-C_{20}$ straight chain alkenylsemicarbazide, $C_2-C_{20}$ straight chain substituted alkenylsemicarbazide, $C_3-C_{50}$ branched chain alkenylsemicarbazide, $C_3-C_{50}$ branched chain substituted alkenylsemicarbazide, $C_3-C_{50}$ cyclic alkenylsemicarbazide, $C_3-C_{50}$ cyclic substituted alkenylsemicarbazide, $C_2-C_{20}$ straight chain alkynylsemicarbazide, $C_2-C_{20}$ straight chain substituted alkynylsemicarbazide, $C_3-C_{50}$ branched chain alkynylsemicarbazide, $C_3-C_{50}$ branched chain substituted alkynylsemicarbazide, $C_3-C_{50}$ cyclic alkynylsemicarbazide, $C_3-C_{50}$ cyclic substituted alkynylsemicarbazide, $C_1-C_{20}$ straight chain alkylthiosemicarbazide, $C_1-C_{20}$ straight chain substituted alkylthiosemicarbazide, $C_2-C_{50}$ branched chain alkylthiosemicarbazide, $C_2-C_{50}$ branched chain substituted alkylthiosemicarbazide, $C_3-C_{50}$ cyclic alkylthiosemicarbazide, $C_3-C_{50}$ cyclic substituted alkylthiosemicarbazide, $C_2-C_{20}$ straight chain alkenylthiosemicarbazide, $C_2-C_{20}$ straight chain substituted alkenylthiosemicarbazide, $C_3-C_{50}$ branched chain alkenylthiosemicarbazide, $C_3-C_{50}$ branched chain substituted alkenylthiosemicarbazide, $C_3-C_{50}$ cyclic alkenylthiosemicarbazide, $C_3-C_{50}$ cyclic substituted alkenylthiosemicarbazide, $C_2-C_{20}$ straight chain alkynylthiosemicarbazide, $C_2-C_{20}$ straight chain substituted alkynylthiosemicarbazide, $c_3-C_{50}$ branched chain alkynylthiosemicarbazide, $C_3-C_{50}$ branched chain substituted alkynylthiosemicarbazide, $C_3-C_{50}$ cyclic alkynylthiosemicarbazide, $C_3-C_{50}$ cyclic substituted alkynylthiosemicarbazide, $C_1-C_{20}$ straight chain alkylhydrazone, $C_1-C_{20}$ straight chain substituted alkylhydrazone, $C_2-C_{50}$ branched chain alkylhydrazone, $C_2-C_{50}$ branched chain substituted alkylhydrazone, $C_3-C_{50}$ cyclic hydrazoalkane, $C_3-C_{50}$ cyclic substituted hydrazoalkane, $C_2-C_{20}$ straight chain alkenylhydrazone, $C_2-C_{20}$ straight chain substituted alkenylhydrazone, $C_3-C_{50}$ branched chain alkenylhydrazone, $C_3-C_{50}$ branched chain substituted alkenylhydrazone, $C_3-C_{50}$ cyclic hydrazoalkene, $C_3-C_{50}$ cyclic substituted hydrazoalkene, $C_2-C_{20}$ straight chain alkynylhydrazone, $C_2-C_{20}$ straight chain substituted alkynylhydrazone, $C_3-C_{50}$ branched chain alkynylhydrazone, $C_3-C_{50}$ branched chain substituted alkynylhydrazone, $C_3-C_{50}$ cyclic hydrazoalkyne, $C_3-C_{50}$ cyclic substituted hydrazoalkyne, $C_1-C_{20}$ straight chain alkylhydrazide, $C_1-C_{20}$ straight chain substituted alkylhydrazide, $C_3-C_{50}$ branched chain alkylhydrazide, $C_3-C_{50}$ branched chain substituted alkylhydrazide, $C_3-C_{50}$ cyclic alkylhydrazide, $C_3-C_{50}$ cyclic substituted alkylhydrazide, $C_2-C_{20}$ straight chain alkenylhydrazide, $C_2-C_{20}$ straight chain substituted alkenylhydrazide, $C_3-C_{50}$ branched chain alkenylhydrazide, $C_3-C_{50}$ branched chain substituted alkenylhydrazide, $C_3-C_{50}$ cyclic alkenylhydrazide, $C_3-C_{50}$ cyclic substituted alkenylhydrazide, $C_2-C_{20}$ straight chain alkynylhydrazide, $C_2-C_{20}$ straight chain substituted alkynylhydrazide, $C_3-C_{50}$ branched chain alkynylhydrazide, $C_3-C_{50}$ branched chain substituted alkynylhydrazide, $C_3-C_{50}$ cyclic alkynylhydrazide and $C_3-C_{50}$ cyclic substituted alkynylhydrazide.

In preferred embodiments, polyamine species are linear or cyclic and are non-aromatic. In still more preferred embodiments, polyamine species are linear or cyclic, non-aromatic, and contain non-amide nitrogen atoms. By non-amide is meant a nitrogen which is not adjacent to a carbonyl group (i.e., C=O or C=S).

In still other embodiments of the present invention compounds having the structure:

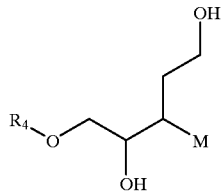

II wherein $R_4$ is an oligonucleotide and M is a pendent group having an amine-containing species attached thereto are provided. The pendent group may be any group to which an amine-containing species may be attached. In preferred embodiments the pendent group is a $R_{10}S^-$ or $R_{10}NH^-$, wherein $R_{10}$ is any of a broad range of reactive groups effective for subsequent attachment of amine-containing species to the pendent group. Suitable for $R_{10}$ are substituted and un-substituted, straight chain or branched chained $C_1$–$C_{20}$ alkyl groups or substituted or un-substituted $C_7$–$C_{14}$ aryl groups having the nucleophile in one position thereon and a further functional group in a further position thereon. The pendent group may thus, subsequently functionalized with a bifunctional linker group amendable for attachment of an amine-containing species to the pendent group. Alternatively the amine-containing species may be directly attached to a pendent group such as by alkylation.

Further in accordance with the present invention are provided compounds having the structure:

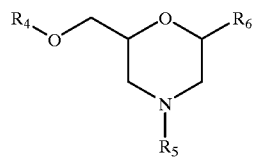

III wherein $R_4$ is an oligonucleotide, $R_5$ is a linear or cyclic amine-containing species containing non-amide nitrogen atoms, and $R_6$ is H, a purine heterocycle or a pyrimidine heterocycle.

The present invention also provides novel amine containing compounds having the structure:

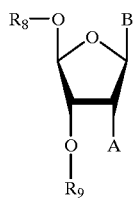

IV wherein B is a purine or pyrimidine heterocycle, $R_8$ and $R_9$ are independently H, $PO_2^-$, a nucleotide, an oligonucleotide or an amine-containing species, and at least one of $R_8$ and $R_9$ is a purine containing oligonucleotide, and at least one of $R_8$, $R_9$ and A is a species comprising the formula $L_1$—$L_2$-polyamine wherein $L_1$ is an amino linker and $L_2$ is a heterobifunctional linker; and wherein if $R_8$ is not a purine containing oligonucleotide or polyamine species, then $R_8$ is a nucleotide or $PO_2^-$; if $R_9$ is not a purine containing oligonucleotide or polyamine species, then $R_9$ is H or a nucleotide; and if A is not a polyamine species then A is H or OH.

Thus $R_8$ and $R_9$ may be oligonucleotides and A may be a species comprising the formula $L_1$—$L_2$-polyamine, or alternatively, $R_8$ may be an oligonucleotide and one or both of $R_9$ and A may be a species comprising the formula $L_1$—$L_2$-polyamine; or $R_9$ may be an oligonucleotide and one or both of $R_8$ and A may be a species comprising the formula $L_1$—$L_2$-polyamine. Furthermore, when $R_8$ is not a purine containing oligonucleotide or polyamine species, then $R_8$ is a nucleotide or $PO_2^-$. If $R_9$ is not a purine containing oligonucleotide or polyamine species, then $R_9$ is H or a nucleotide, and if A is not a polyamine species then A is H or OH.

In preferred embodiments of the present invention commercially available amino linkers may be used. For example, the 3'-amino modifiers having the trade names C3 CPG and C7 CPG available through Glen Research may be employed. 5'-Amino modifiers may also be used such as C3 and C7 5' branched modifiers available through Glen Research. Similarly, 2'-amino modifiers are also envisioned for use in some aspects of the present invention, see. e.g.. U.S. application Ser. No. 782,374, filed Oct. 24, 1991. The amino linkers are designed to functionalize a target oligonucleotide by the introduction of a primary amine at a designated site, be it 2', 3' or 5'. As will be apparent to one skilled in the art, any linker which meets this end is encompassed by the present invention.

Likewise, bifunctional linkers effective for purposes of the present invention are available commercially. For example, bis-(maleimido)-methyl ether (BMME), disuccinimidyl suberate (DSS), 3-maleimidobenzoyl-N-hydroxysuccinimide (MBS), maleimidohexanoyl-N-hydroxylsuccinimide (MHS) and N-succinimidyl-3-(2-pyridyldithio) propionate (SPDP) may be useful in some embodiments of the present invention. Other useful bifunctional linkers will be apparent to one skilled in the art as for instance from Pierce, Rockford, Ill.

Compounds of the present invention may be prepared by providing an oligonucleotide comprising one or more abasic sites. In the context of the present invention "abasic site" refers to a nucleotide unit in which the purine or pyrimidine group has been removed or replaced by a group such as a hydroxyl group. One or more abasic sites may be incorporated into one or more nucleotide bases of an oligonucleotide to form a synthon having the structure:

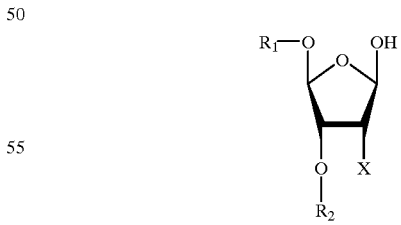

wherein $R_1$ and $R_2$ are independently H, a nucleotide, an oligonucleotide, or amine-containing species, and at least one of $R_1$ and $R_2$ is a purine containing oligonucleotide, and X is H, O—$R_{11}$, S—$R_{11}$, F, Cl, Br, CN, $CF_3$, $OCF_3$, OCN, $SOCH_3$, $SO_2CH_3$, $ONO_2$, $N_3$, $HN_2$, heterocylcoalkyl, heterocycloalkaryl, aminoalkylamino, polyalkylamino, substituted silyl, a reporter molecule, an RNA cleaving group, a group for improving the pharmacokinetic properties of an oligonucleotide, or a group for improving the pharmacodynamic properties of an oligonucleotide wherein $R_{11}$ is H, $C_1$ to $C_{10}$ straight or branched chain lower alkyl or substituted lower alkyl, $C_2$ to $C_{10}$ straight or branched chain lower alkenyl or substituted lower alkenyl, $C_3$ to $C_{10}$ straight or branched chain lower alkynyl or substituted lower alkynyl, a $^{14}C$ containing lower alkyl, lower alkenyl or lower alkynyl, $C_7$ to $C_{14}$ substituted or unsubstituted alkyaryl or aralkyl, a $^{14}C$ containing $C_7$ to $C_{14}$ alkaryl or aralkyl, alicyclic, heterocyclic, a reporter molecule, a RNA cleaving group, a group for improving the pharmacokinetic properties of an oligonucleotide or a group for improving the pharmacodynamic properties of an oligonucleotide.

An enzymatic process may be used to produce such a synthon having abasic sites by reaction of a DNA glycosylase with an oligonucleotide starting material. Several glycosylase enzymes are available, see Friedberg, DNA Repair (W. H. Freeman and Company, NY, 1985) p. 153. For example, uracil DNA glycosylase act on uracil bases within an oligonucleotide to create abasic sites. Of course, it should be recognized that enzymatic methods using DNA glycosylase may be less effective for oligonucleotides more closely resembling RNA such as oligonucleotides having 2' modifications.

Enzymes, as employed in the present invention, may be derived from naturally occurring sources or may be prepared by recombinant techniques. Many useful enzymes are available commercially.

Synthons alternatively can be prepared by incorporation of abasic sites into an oligonucleotide via abasic sugar precursors. For example, 5-O-(4,4'-dimethoxytrityl)-1,2-dideoxy-1-(o-nitrobenzyl)-D-ribofuranose-3-O-(2-cyanoethyl-N,N'-diisopropyl) phosphoramidite may be prepared by modification of the procedures of Lyer, et al., *Nucleic Acids Research* 1990, 18, 2855 and Didier, et al., *Tetrahedron Letters* 1991, 32, 207. Phosphoramidites having a 2' substitutions and abasic sites may also be prepared. For example, a synthon may have 2'-O-methyl or 2'-fluoro substitutions. Such phosphoramidite may be incorporated into an oligonucleotide by standard procedures. An o-nitrobenyzldeoxyfuranose containing oligonucleotide can be synthesized in accordance with these procedures. Post synthesis photolysis utilizing a high intensity Hg lamp generates the corresponding abasic site-containing polymer. In addition, other methods of introducing abasic sites at the 3', 5' and internal positions of an oligonucleotide to form a synthon are known to those skilled in the art. Thereafter the synthon may be reacted with an amine-containing species under reducing conditions. As illustrated in FIG. 1, Step A, a compound may be prepared wherein B is uridine and an enzymatic process may be used to produce a synthon having abasic sites at one or more uridine sites by digestion of the compound with an enzyme such as uracil-DNA glycosylase. Other glycosylases will be effective for different targets. As described above, a glycosylase may be determined by the combined sequence of $R_1$, $R_2$ and B. Some useful glycosylases and their respective targets are described, for example, by Friedberg, DNA Repair (W. H. Freeman and Company, NY, 1985) p. 153. These enzymes are commercially available or may be prepared from known procedures in the art.

Figure 2:
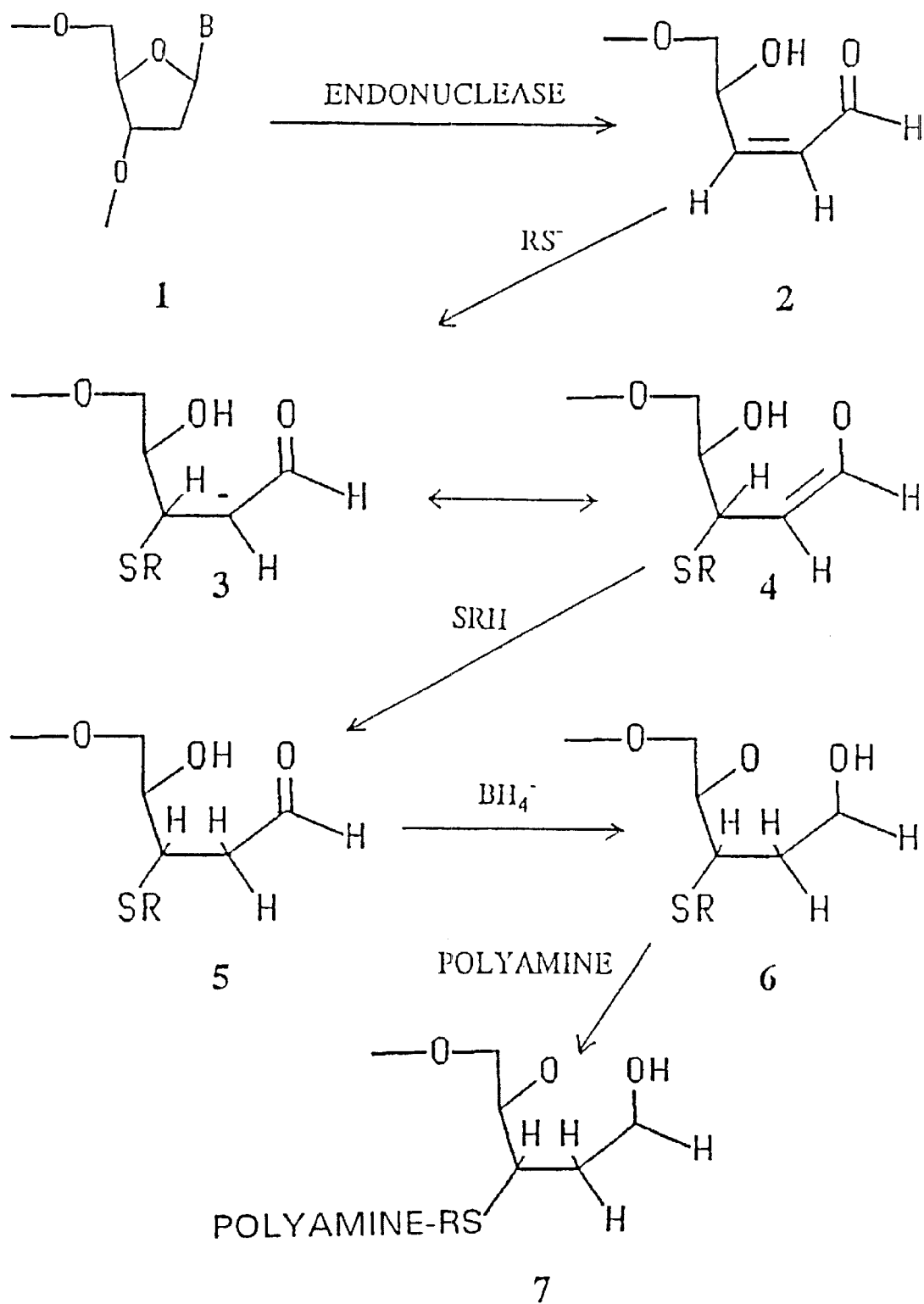
FIG. 2 is a schematic representation of one preferred syntheses of compounds of Formula II.

In other embodiments of the present invention, as exemplified in FIG. 2, compounds having Formula II may be prepared by providing starting material having the structure:

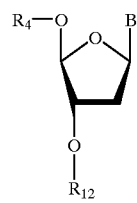

wherein $R_4$ is an oligonucleotide, $R_{12}$ is an oligonucleotide and B is urea or a heterocyclic base having a corresponding glycosylase and reacting the compound with an endonuclease to produce the compound 2 as described by Manoharan, et al., *J. Am. Chem. Soc,* 1988, 110, 2690. Thereafter, the compound 2 is contacted with a pendent group such as $R_{10}S^-$, and reduced with the reducing agent $NaCNBH_4$ to stabilize the product 5. An amine-containing species may then be added such as by alkylation to provide the final product 7. An amine-containing species may alternatively be added directly to a bifunctional pendent group. Some endonucleases which will be useful in embodiments of the present invention are described, for example, in Doetsch et al., *Mutation Research* 1990, 236, 173, incorporated by reference herein in its entirety. The endonuclease chosen will depend upon the identity of B and the sequence of $R_4$ and/or $R_{12}$. Thus, if B is a pyrimidine heterocycle, and the sequence of $R_{12}$ begins with a pyrimidine, then an endonuclease such as T4 or *M. luteus* UV endonuclease may be chosen. Following digestion by T4 or *M. luteus* UV endonuclease, B and $R_{12}$ are removed, resulting in a 3' terminal α,β unsaturated aldehydic species. In some instances, it may be desirable to engineer the sequence of the species so as to provide a endonuclease digestion site at a desired location.

Thus, in one preferred embodiment of the present invention $R_4$ may be TGGGAGCCATAGCGAGGCUCG (SEQ ID NO: 1), B may be the pyrimidine thymine and $R_{12}$ may be a thymidine dinucleotide. The net result of digestion of this species with T4 UV endonuclease will be TGGGAGC-CATAGCGAGGCN (SEQ ID NO: 2) wherein N represents the aldehydic species.

Treatment of the digested compound with pendent group comprising a linker bearing a nucleophile results in the addition of the pendent group at the 3' terminus of the compound to join the linker to the digested compound. Suitable nucleophilic species include thiols and amines moieties as described above. In preferred embodiments of the present invention the pendent group is $R_{10}S^-$ or $R_{10}NH^-$. A polyamine species such as $NH_2(CH_2)_nNH_2$ wherein n is an integer from 1 to about 10 could be used as the attacking nucleophile by suitably blocking one end thereof and utilizing the other end as the attacking nucleophilic species. $R_{10}$ can be further selected to provide a linkage or bridge between the nucleophile and an amine-containing species. Suitable for $R_{10}$ are substituted and un-substituted, straight chain or branched chained $C_1$–$C_{20}$ alkyl groups or substituted or un-substituted $C_7$–$C_{14}$ aryl groups having the nucleophile in one position thereon and a further functional group in a further position thereon. After attachment of the pendent group via nucleophilic attack on compound 2, for attachment of the amine-containing species the further functional group is then derivitized either via a bi-functional linking group, an alkylation type reaction or other derivation reaction known to those skilled in the art.

Upon addition of the pendent group to the digested compound, the double bond remaining on the digested compound is reduced to stabilize the product. Reducing agents effective to stabilize the end product of such a reaction are well known in the art. Some suitable reducing agents include sodium cyanoborohydride, lithium cyanoborohydride and sodium borohydride.

Thereafter an amine-containing species may be added via an alkylation reaction or directly to a pendent group which is a bifunctional linker. The compound may further be derivatized by attaching one or more reactive groups to at least one of the nitrogen atoms of the amine-containing species. Reactive groups include, but are not limited to reporter groups, alkylating agents, intercalating agents, RNA cleaving moieties, cell receptor binding molecules, steroids, peptides, crown amines, porphyrins and cross-linking agents.

In accordance with other methods of the present invention compounds of Formula III may be prepared by reacting an oligonucleotide having a 3' ribofuranosyl sugar with an oxidizing agent to produce an dialdehyde-terminated activated oligonucleotide. Suitable oxidants include periodate solution, lead tetraacetate, activated $MnO_2$, thallium (III) salts, pyridinium chlorochromate and $O_3$ catalyzed by Co (III) salts.

Thereafter the dialdehyde-terminated activated oligonucleotide is reacted with an amine-containing species under reducing conditions. Reducing agents are known to those skilled in the art. Preferably, the activated oligonucleotide and species containing at least one nitrogen atom will be reacted in the presence of a solution of sodium cyanoborohydride, lithium cyanoborhydride or sodium borohydride.

Figure 3:
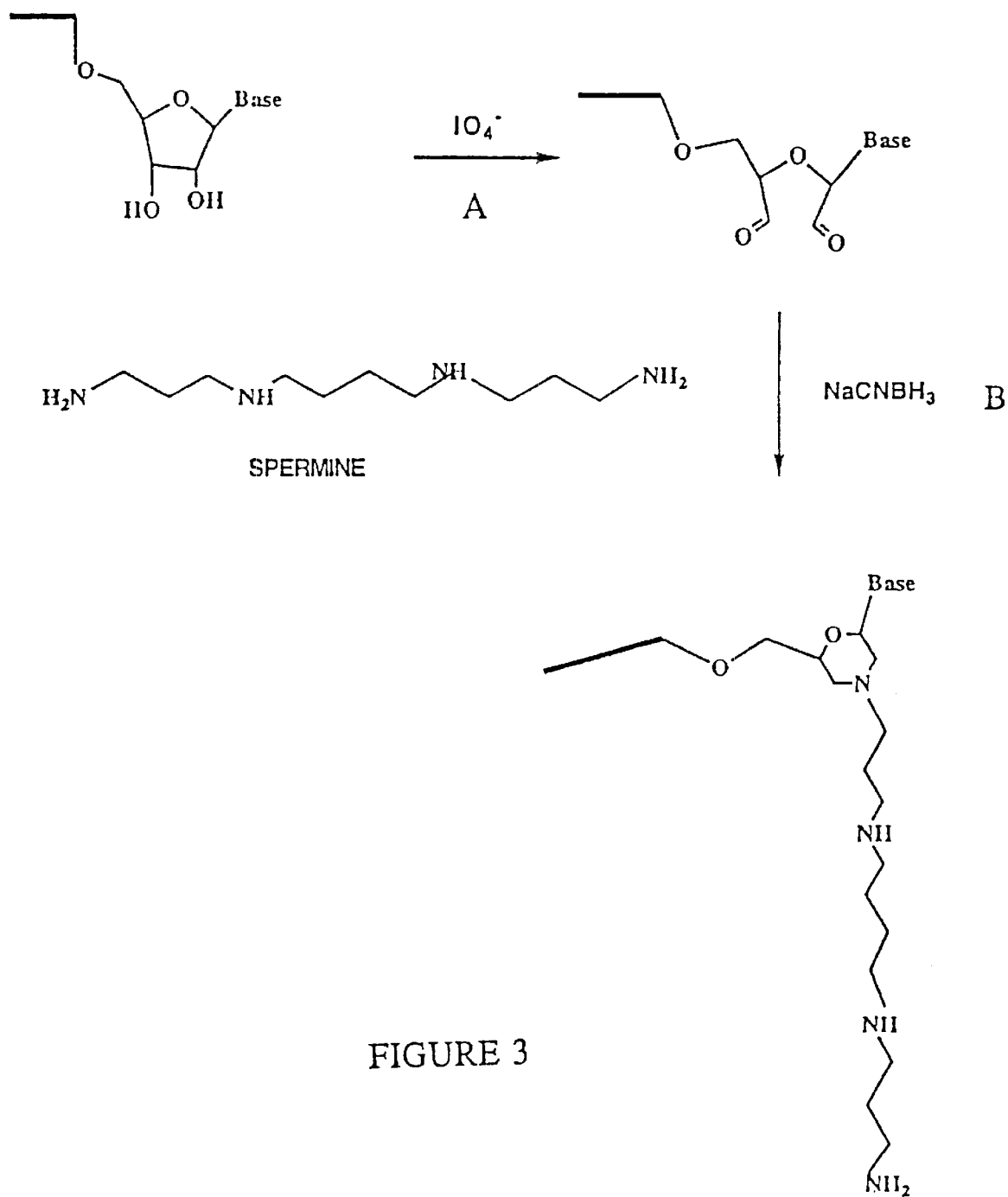
FIG. 3 is a schematic representation of one preferred syntheses of compounds of Formula III.

In preferred embodiments of the present invention compounds may be produced as illustrated by FIG. 3, by preparation of an oligonucleotide having a 3' ribofuranosyl end followed by attack of the 3' ribofuranosyl ring by an oxidant such as m-periodate solution in 0.1M NaOac buffer pH5, as described by Bayard, et al., *Biochemistry* 1986, 25, 3730 to produce a dialdehyde-terminated activated oligonucleotide (FIG. 3, Step A). The activated oligonucleotide and a species containing four nitrogen atoms, spermine, can be reacted in the presence of the reducing agent, sodium cyanoborohydride (FIG. 3, Step B).

Compounds of the present invention preferably are specifically hybridizable with a target region. By "specifically hybridizable" herein is meant capable of forming a stable duplex with a target DNA or RNA. It is believed that oligonucleotides which form Watson-Crick base pairs, i.e., are complementary with target DNA or RNA and which specifically hybridize with target DNA or RNA, inhibit the flow of genetic information from DNA to protein. In some embodiments of the present invention the oligonucleotide portions of compounds of the present invention are at least 70% complementary to a target sequence. In preferred embodiments of the present invention the oligonucleotide portions of compounds of the present invention are at least 80% complementary to a target sequence. Full (100%) complementarity of the oligonucleotide portions of compounds of the present invention to a target sequence is most preferred. In preferred embodiments of the present invention, the oligonucleotide portions may be specifically hybridizable with DNA or RNA from papilloma virus, herpes viruses, human immunodeficiency virus, Candida, cytomegaloviruses, and influenza viruses. In addition, the oligonucleotide portions may also be specifically hybridizable with endogenous DNA or RNA of a cell. By oligonucleotide portions is meant $R_1$ and/or $R_2$ of Formula I, $R_4$ of Formula II, $R_4$ and/or $R_6$ of Formula III, or $R_8$ and/or $R_9$ of Formula IV. For therapeutics, an animal suspected of having a disease characterized by excessive or abnormal production of a protein is treated by administering a compound having the structure set forth in Formula I, Formula II, Formula III, or Formula IV in a pharmaceutically acceptable carrier. Most preferable, the compound is hybridizable with an RNA coding for the protein. Persons of ordinary skill in the art can easily determine optimum dosages, dosing methodologies and repetition rates. Such treatment is generally continued until either a cure is effected or a diminution in the diseased state is achieved. Long term treatment is likely for some diseases.

The compounds of the present invention will also be useful as a research reagent useful for the modulation of the production of a protein by an organism. Modulation may be accomplished by contacting the organism with compounds of the present invention having structures as set forth in Formula I, Formula II, Formula III, or Formula IV. Preferably the compounds are hybridizable with RNA coding for the protein.

Diagnostic applications include the detection of the presence or absence of an RNA in a sample suspected of containing RNA comprising contacting the sample with a compound having structures as set forth in Formula I, Formula II, Formula III or Formula IV wherein the compound is specifically hybridizable with the RNA and detecting the presence or absence of hybridization of the compound to the sample wherein hybridization is indicative of the present of the RNA in the sample.

It is also envisioned by the present invention to provide compounds in which at least one of the nitrogen atoms of the polyamine are derivatized with one or more of the group consisting of functionalities such as reporter groups, alkylating agents, intercalating agents, cell receptor binding molecules, steroids, crown amines, porphyrins, PNA (Peptide Nucleic Acids), PEG (polyethylene glycol) containing amines, amines and cross-linking agents. Therapeutic, diagnostic and research reagent applications are equally, or even more effective when the polyamine species further comprises such groups. Such compounds allow greater numbers of functionalities to be delivered to a target. For example, reporter groups such as biotin, fluorescent molecules and various fluorophores may be attached to compounds of the present invention to effect diagnostic ends, resulting in signal amplification as compared to conventional oligonucleotide-reporter group combinations. In a preferred embodiment of the present invention, biotin may be used to functionalize compounds of the present invention by reacting a compound with D-biotin-N-hydroxysuccinimide ester. In a further preferred embodiment, the polyamine species may be further functionalized by reacting the compound containing the polyamine species with an activated ester having the structure (Compound 13):

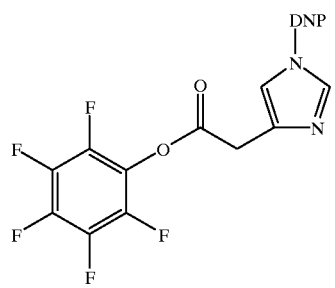

Where DNP stands for 2,4-dinitrophenyl protecting group to form a compound with repeating imidazole catalytic cleaver units useful as an antisense therapeutic agents. Heterobifunctional linkers also can be utilized for attachment of intercalators, RNA cleaving agents including imidazoles, cell receptor binding molecules, steroids, alkylating agents, crown amines, porphyrins and cross-linkers to the polyamine species.

The following examples are illustrative but are not meant to be limiting of the present invention.

EXAMPLE 1
Preparation of an Abasic Site Containing Oligonucleotide Via Enzymatic Reaction A. Synthesis of an Oligonucleotide containing a Single Uridine Site An oligonucleotide having the sequence CGC AGU CAG CC (SEQ ID NO:3) wherein U represents a 2'deoxyuridine nucleotide, was prepared by standard solid phase synthesis. The deoxyuridine nucleotide in the middle of the sequence was added during synthesis utilizing deoxyuridine phosphoramidite (Glen Research, Sterling, Va.). The oligonucleotide was prepared utilizing standard synthesis cycles. It was deprotected by normal deprotection at 55° C. utilizing ammonium hydroxide, 30%, for 16 hours. The solvent was evaporated and the residue was purified by HPLC and detritylated. Final purification was effected on Sephadex G-25.

B. Preparation of Enzyme Stock Solution

Uracil-DNA glycosylase was isolated from *E. Coli* M5219 cells transformed with the expression plasmid pBD396 containing the ung gene. The enzyme was purified by electrophoretic homogeneity as described by Lindahl, et al., *J. Biol. Chem.* 1977, 252, 3286 and stored in 30 mM HEPES-NaOH, pH 7.4, containing 5% glycerol, 2 mM DTT and 1 mM EDTA.

C. Preparation of Oligonucleotide Containing Single Abasic Site

An abasic oligonucleotide of the sequence CGC AGN CAG CC (SEQ ID NO:4) wherein N represents an abasic site, was prepared by treating 237 O.D. units of an oligonucleotide having SEQ ID NO:1 of Example 1A in 0.5 ml water with 200 $\mu$l of the stock solution of Example 1B (200 $\mu$g of uracil DNA-glycosylase) and incubating at room temperature overnight. HPLC analysis showed quantitative removal of uracil as indicated by a 1:10 ratio between uracil and the abasic dodecamer oligonucleotide. The uracil retention time was 2.43 minutes and the abasic oligonucleotide was 21.68 minutes. The solution was lyophilized and stored in the freezer until further use.

D. Preparation of Oligonucleotide Containing Multiple Uridine Sites

In the manner of Example 1A the following oligonucleotide was prepared GAC AGA GGU AGG AGA AGU GA (SEQ ID NO: 5) wherein U represents a 2'-deoxyuridine nucleotide. The oligonucleotide is treated in accordance with the procedure of Example 1C resulting in an oligonucleotide of the sequence GAC AGA GGN AGG AGA AGN GA (SEQ ID NO: 6) wherein N represents an abasic site within the oligonucleotide.

EXAMPLE 2
Preparation of an Abasic Site Containing Oligonucleotide Via an Abasic Sugar Precursor A. Preparation of 5-O-4,4'-Dimethoxytrityl-1,2-Dideoxy-1-(o-nitrobenzyl)-D-Ribofuranose-3-O-(2-Cyanoethyl-N,N'-Diisopropyl) Phosphoramidite 5-O-4,4'-dimethoxytrityl-1,2-dideoxy-D-ribofuranose-3-O-(2-cyanoethyl-N,N'-diisopropyl) phosphoramidite is prepared in accordance with modification of the procedures of Lyer, et al., *Nucleic Acids Research* 1990, 18, 2855 and Didier, et al., *Tetrahedron Letters* 1991, 32, 207 incorporated by reference herein in their entireties.

B. Preparation of Oligonucleotide Containing Abasic Site

Oligonucleotide having the sequence CGC AGN CAG CC wherein N represents an abasic site (SEQ ID NO:4) from Example IC can be prepared in accordance with modifications of the procedures of Lyer, et al., *Nucleic Acids Research* 1990, 18, 2855 and Didier, et al., *Tetrahedron Letters* 1991, 32, 207. In accordance with these procedures, an o-nitrobenzyl deoxyfuranose containing oligonucleotide is synthesized using the oligonucleotide synthetic methods of Lyer, et al., and Didier, et al., Photolysis utilizing a high intensity Hg lamp (300 nm) generates the corresponding abasic site containing oligonucleotide. Such abasic oligonucleotides are also described in Horn, et al., *Nucleosides and Nucleotides* 10:299 (1991).

EXAMPLE 3
Preparation of Modified Abasic Sugar Precursors

A. Preparation of 5-O-(4,4'-Dimethoxytrityl)-2-O-Methyl-1,2-dideoxy-D-Ribofuranose-3-O-(2-Cyanoethyl-N,N'-Diisopropyl) Phosphoramidite 1-O-methyl-D-ribofuranose is 3,5 protected with TIPS-Cl$_2$. It is then 2-position methylated with either diazomethane or methyl iodide/silver oxide (CH$_3$I/Ag$_2$O). The composition is then treated with an acetic anhydride/acetic acid/sulfuric acid mixture to give a 1-O-acetyl, 2-O-methyl 3,5 protected sugar. The 1-O-acetyl, 2-O-methyl 3,5 protected sugar is deprotected with tetrabutyl ammonium fluoride, 5-position dimethoxytritylated, and 3-position phosphitylated. Thereafter, this phosphoramidite may be incorporated into an oligonucleotide by standard phosphoramidite procedures and ammonia deprotected to form a 2'-O-methyl, 1' abasic site containing oligonucleotide.

B. Preparation of 5-O-4,4'-Dimethozytrityl-2-o-Methyl-1,2-Dideoxy-1-(o-nitrobenzyl)-D-Ribofuranose-3-O-(2-Cyanoethyl-N,N'-Diisopropyl) Phosphoramidite 1-O-acetyl 2,3,5-tri-O-benzoyl-D-ribofuranose is condensed with o-nitrobenzyl alcohol under Vorbruggen conditions. The resultant 1-O-(ortho-nitrobenzyl)-2,3,5-tri-O-benzoyl ($\alpha$,$\beta$)-D-ribofuranose is deprotected with ammonia and subsequently treated with TIPS-Cl$_2$. The resultant 3,5-silyl protected 1-O-(ortho-nitro benzyl) D-ribofuranose is reacted with diazomethane or CH$_3$I/Ag$_2$O to give the required 2-O-methyl compound. Subsequent 3,5-deprotection, 5-dimethoxy tritylation and 3-phosphitylation gives the named phosphoramidite. The phosphoramidite can be incorporated into an oligonucleotide via standard phosphoramidite procedures.

C. Preparation of 5-O-(4,4-Dimethoxytrityl)-2-Fluoro-1,2-Dideoxy-D-Ribofuranose-3-O-(2-Cyanoethyl-N,N'-Diisopropyl) Phosphoramidite 1-O-(ortho-nitrobenzyl)-2,3,5-tri-O-benzoyl-D-ribofuranose is deprotected at 2,3,5 positions using ammonia. Tritylation with excess trityl chloride/pyridine/4-dimethylaminopyridine gives 3-5-ditrityl-1-O-nitrobenzyl-D-ribofuranose. Oxidation at 2 position with CrO$_3$ followed by NaBH$_4$ reduction inverts the configuration at 2 position yielding an arabino sugar. The arabino sugar is converted to its triflate at 2 position and the triflate is displaced with fluoride ion to yield the 2-fluoride modified sugar which can be 5 position protected and phosphitylated to incorporate the sugar into an oligonucleotide via standard oligonucleotide synthesis.

EXAMPLE 4

Oligonucleotides conjugated in the following example are set forth in Table 2.

TABLE II

| OLIGOMER (SEQ ID NO.) | TARGET | SEQUENCE | LINKER (L) | OTHER MODIFI- CATIONS |
|---|---|---|---|---|
| A (SEQ ID NO:7) | ICAM | TGG GAG CCA TAG CGA GGC—L | 3-carbon amino | P = S |
| B (SEQ ID NO:7) | ICAM | TGG GAG CCA TAG CGA GGC—L | 3-carbon amino | P = O |
| C (SEQ ID NO:8) | BPV | CTG TCT CCA* TCC TCT TCA CT | 2'amino-pentoxy | P = O |
| D (SEQ ID NO:9) | BPV | CTG TCT CCA TCC TCT TCA CT—L | 3-carbon amino | P = O |
| E (SEQ ID NO:9) | BPV | CTG TCT CCA TCC TCT TCA CT—L | 6-carbon amino | P = O |
| F (SEQ ID NO:10) | CMV | GGC GUC UCC AGG CGA UCU GAC* | | 2'-OMe |
| G (SEQ ID NO:11) | ICAM | TCT GAG TAG CAG AGG AGC TC* | | 2'-OMe |
| H (SEQ ID NO:12) | | GGA UGG CGU CUC CAG GCG AUC* | | 2'-OMe |
| I (SEQ ID NO:13) | | GGA UGG CGU CUC CAG GCG AUC—L | 3-carbon amino | 2'-OMe |
| J (SEQ ID NO:13) | | GGA UGG CGU CUC CAG GCG AUC—L | 6-carbon amino | 2'-OMe |
| K (SEQ ID NO:7) | | F—TGG GAG CCA TAG CGA GGC—L | 3-carbon amino | 2'-OMe |

A* = 2'-O-aminopentoxy-2'-deoxyadenosine
C* = 2'-aminopropoxy cytosine
F = Fluorescein A. 3' Terminus Polyamine End Labeled Oligonucleotide.
1. 3'-Terminus Polyamine Oligonucleotide I Polyamines were attached to the 3'-terminus end of a phosphodiester oligonucleotide having the sequence D-polyamine [(SEQ ID NO: 9)-polyamine], wherein the polyamine is one of the following:

TABLE III

| 1,6 Diaminohexane | Oligomer D(i) |
|---|---|
| Diethylenetriamine | Oligomer D(ii) |
| Triethylenetetramine | Oligomer D(iii) |
| Spermine | Oligomer D(iv) |
| Pentaethylenehexamine | Oligomer D(v) | a. Preparation of the Intermediate Linker

The oligonucleotide sequence having a 3'-terminus amino group was synthesized using 3'-amino modifier (with a three carbon linker) controlled pore glass (CPG) from Glen Research as the solid support. The synthesis was conducted with an Applied Biosystems 380B or 994 in the "Trityl-Off" mode. The resultant oligonucleotide was cleaved from the solid support and deprotected with concentrated $NH_4OH$ for 16 hrs at 55° C. Purification on a Sephadex G-25 column yielded a 3'-amino modified oligonucleotide of the specified sequence.

b. Preparation of Polyamine Functionalized Oligonucleotide

The crude 3'-aminolinker-oligonucleotide (SEQ ID NO:9) (15 O.D. units, approximately 85 nmols) was dissolved in freshly prepared $NaHCO_3$ buffer (150 ul, 0.2 M, pH 8.1) and treated with a solution of disuccinimidyl suberate (DSS) (approximately 5 mgs) dissolved in 150 ul of methyl sulfoxide (DMSO). The reaction mixture was left to react for 20 minutes at room temperature. The mixture was then passed over a Sephadex G-25 column (0.7×45 cm) to separate the activated oligonucleotide-DSS from the excess DSS. The oligonucleotide-DSS was then frozen immediately and lyophilized to dryness. A solution of polyamine in 0.33 M NaOAc (approximately 6 mg polyamine in 300 ul 0.33 M NaOAc, pH 5.2, final solution pH 6–8.0) was added to the dried oligonucleotide-DSS, and this mixture was allowed to react overnight at room temperature. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using a Water's Delta-Pak C-18 reverse phase column. HPLC retention times were as set forth in Table 4.

TABLE IV

| Oligomer | Retention Time |
|---|---|
| unreacted D | 26.44 mins |
| Oligomer D(i) | 27.48 mins |
| Oligomer D(ii) | 27.23 mins |
| Oligomer D(iii) | 27.27 mins |
| Oligomer D(iv) | 27.54 mins |
| Oligomer D(v) | 27.36 mins |

In a second test run under the same conditions the HPLC gradient was 0–10 mins, 95% solvent A, 5% solvent B;

linear increase to 15% solvent B in 60 minutes. HPLC retention times were as set forth in Table 5.

TABLE V

| Oligomer | Retention Time |
| --- | --- |
| untreated D | 60.74 mins |
| Oligomer D(ii) | 62.37 mins |
| Oligomer D(v) | 65.24 mins |

Gel analysis showed progressively slower migration 30 times for the polyamine conjugates (the larger the polyamine, the slower the migration) versus the oligonucleotide alone. (Gel: 313-107)

c. Nuclease Stability of 3' Polyamine Conjugates in Fetal Calf Serum

Polyamine conjugates of the invention are assessed for their resistance to serum nucleases by incubation of the oligonucleotides in media containing various concentrations of fetal calf serum. Labeled oligonucleotides are incubated for various times, treated with protease K and then analyzed by gel electrophoresis on 20% polyacrylamide-urea denaturing gels and subsequent autoradiography or phosphor-imaging. Autoradiograms are quantitated by laser densitometry. Based upon the location of the modifications and the known length of the oligonucleotide it is possible to determine the effect of the particular modification on nuclease degradation. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified and the modified oligonucleotides. The $t_{1/2}$ are set forth below.

TABLE VI

| Oligonucleotide | $t_{1/2}$ (hours) |
| --- | --- |
| wild type oligomer D | 0.5 (no aminolinker) |
| unreacted oligomer D | 22 (with aminolinker) |
| oligomer D(ii) | 48 |
| oligomer D(v) | >50 |

2. 3'-Terminus Polyamine Conjugate II

Polyamines were attached to the 3'-terminus end of a phosphodiester oligonucleotide having the sequence E-polyamine [(SEQ ID NO: 9)-polyamine] wherein the polyamine is one of the following:

TABLE VII

| Diethylenetriamine | Oligomer E(i) |
| --- | --- |
| Pentaethylenehexamine | Oligomer E(ii) | a. Preparation of the Intermediate Linker

The intermediate linker was prepared as described in Example 4-A-1-a substituting a 3' amino modifier with a six carbon linker (Clonetech, Palo Alto, Calif.) for the 3'-amino modifier (with a three carbon linker.

3. Preparation of Polyamine Functionalized Oligonucleotide

The polyamine functionalized oligonucleotide was prepared in accordance with Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B;

linear increase to 25% solvent B in the next 50 minutes using a Water's Delta-Pak C-18 reverse phase column. HPLC retention times were as set forth in Table 8.

TABLE VIII

| Oligomer | Retention Time |
| --- | --- |
| untreated E | 41.38 mins |
| Oligomer E(i) | 43.29 mins |
| Oligomer E(ii) | 43.43 mins |

Gel analysis showed progressively slower migration times for the polyamine conjugates (the larger the polyamine, the slower the migration) versus the oligonucleotide alone. (Gel: 353-35).

4. 3'-Terminus Polyamine Conjugate III

Polyamines were attached to the 3'-terminus end of a phosphorothioate oligonucleotide having the sequence A-polyamine [(SEQ ID NO:7)-polyamine] where the polyamine is one of the following:

TABLE IX

| 1,6 Diaminohexane | Oligomer A(i) |
| --- | --- |
| Diethylenetriamine | Oligomer A(ii) |
| Triethylenetetramine | Oligomer A(iii) |
| Spermine | Oligomer A(iv) |
| Pentaethylenehexamine | Oligomer A(v) | a. Preparation of the Intermediate Linker

The intermediate linker was prepared as descried in Example 4-A-1-a utilizing the Beaucage reagent (3H-1,2-benzodithioate-3-one 1,1-dioxide, Radhakrishnan, et al., *J. Am. Chem. Soc.* 1990, 112, 1253) to form the phosphorothioate inter-nucleotide backbone. The 3'-aminolinker was introduced as described in example 4-A-1-a.

b. Preparation of Polyamine Functionalized Oligonucleotide

Oligonucleotides were functionalized as described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using a Water's Delta-Pak C-18 reverse phase column. HPLC retention times were as set forth in Table X.

TABLE X

| Oligomer | Retention Time |
| --- | --- |
| unreacted A | 30.77 mins |
| Oligomer A(iii) | 31.31 mins |
| Oligomer A(v) | 31.02 mins |

In a second test run under the same conditions, the HPLC gradient was 0–10 mins, 95% solvent A, 5% solvent B; linear increase to 15% solvent B in 60 minutes. Retention times were as set forth in Table XI.

TABLE XI

| Oligomer | Retention Time |
| --- | --- |
| untreated A | 68.62 mins |
| oligomer A(i) | 68.70 mins |
| oligomer A(ii) | 68.69 mins |

In a second test run under the same conditions, HPLC retention times were as set forth in Table XII.

TABLE XII

| Oligomer | Retention Time |
| --- | --- |
| untreated A | 30.34 mins |
| Oligomer A(iv) | 30.57 mins |
| Oligomer A(v) | 30.72 mins |

Gel analysis showed progressively slower migration times for the polyamine conjugates (the larger the polyamine, the slower the migration) versus the oligonucleotide alone. (Test run 1 Gel, 313-82; Test run 2 Gel, 285-138; Test run 3 Gel, 353-57)

C. Preparation of Biotin Functionalized Oligonucleotide Polyamine Conjugate

To further characterize the oligonucleotide polyamine conjugate, biotin was attached to the free amines made available by the polyamines attached in Example 4-A-4-b. About 10 O.D. units ($A_{260}$) of Oligomers A(i) and A(ii) (approximately 58 nmoles) were dried in a microfuge tube. The oligonucleotide polyamine conjugate was rehydrated in 400 ul of 0.2 M $NaHCO_3$ (pH 8.1) buffer and D-biotin-N-hydroxysuccinimide ester (approximately 5.0 mgs biotin for the 1,6 Diaminohexane conjugate, 8.0 mgs for the Diethylenetriamine) (Sigma) was added followed by 200 ul of DMF. The solution was left to react overnight at room temperature. The solution was then passed over a NAP-25 column and analyzed by reverse phase HPLC. Solvent A was 50 mM TEAA and solvent B was $CH_3CN$. The HPLC gradient was 0–10 mins, 95% A, 5% B; linear increase to 40% B in the next 50 minutes using a Water's Delta-Pak C-18, reverse phase column. The HPLC retention times were as set forth in Table XIII.

TABLE XIII

| Oligomer | Retention Time |
| --- | --- |
| untreated A | 30.77 mins |
| Oligomer A(i) | 31.31 mins |
| Oligomer A(i)-Biotin | 35.56 mins |
| Oligomer A(ii) | 31.02 mins |
| Oligomer A(ii)-Biotin | 36.23 mins |

5. 3'-Terminus Polyamine Conjugate IV

Polyamines were attached to the 3'-terminus end of the phosphodiester oligonucleotide having the sequence B-polyamine [(SEQ ID NO: 7)-polyamine] wherein the polyamine is one of the following:

TABLE XIV

| | |
| --- | --- |
| Diethylenetriamine | Oligomer B(i) |
| Triethylenetetramine | Oligomer B(ii) |
| Spermine | Oligomer B(iii) |
| Pentaethylenehexamine | Oligomer B(iv) | a. Preparation of the Intermediate Linker

The intermediate linker was prepared as described in Example 4-A-1-a.

b. Preparation of Polyamine Functionalized Oligonucleotide

The oligonucleotide was functionalized with polyamines as described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using a Water's Delta-Pak C-18 reverse phase column. HPLC retention times were as set forth in Table XV.

TABLE XV

| Oligomer | Retention Time |
| --- | --- |
| untreated B | 25.71 mins |
| Oligomer B(i) | 26.11 mins |
| Oligomer B(ii) | 25.26 mins |
| Oligomer B(iii) | 25.10 mins |
| Oligomer B(iv) | 25.12 mins |

Gel analysis showed progressively slower migration times for the polyamine conjugates (the larger the polyamine, the slower the migration) versus the oligonucleotide alone. (Gel: 313-112)

B. 2' Internal Polyamine Labeled oligonucleotide 1. 2'-Internal Polyamine Oligonucleotide I Polyamines were attached to the 2'-internal linker site of a phosphodiester oligonucleotide having the sequence C-polyamine [(SEQ ID NO: 8)-polyamine] wherein the polyamine is one of the following:

TABLE XVI

| | |
| --- | --- |
| Diethylenetriamine | Oligomer C(i) |
| Triethylenetetramine | Oligomer C(ii) |
| Pentaethylenehexamine | Oligomer C(iii) | a. Preparation of the Intermediate Linker

The intermediate linker was prepared as described in Example 4-A-1-a incorporating a modified adenosine phosphoramidite (with a 2'-aminolinker) at position #9. This oligonucleotide and the 2'-amino linker have been described in Manoharan, et al., *Tetrahedron Letters* 1991, 32, 7171.

b. Preparation of Polyamine Functionalized Oligonucleotide

The oligonucleotide was functionalized as described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using a Water's Delta-Pak C-18 reverse phase column. HPLC retention times were as set forth in Table XVII.

TABLE XVII

| Oligomer | Retention Time |
| --- | --- |
| untreated C | 26.20 mins |
| Oligomer C(i) | 27.52 mins |
| Oligomer C(ii) | 27.50 mins |
| Oligomer C(iii) | 27.59 mins |

Gel analysis showed progressively slower migration times for the polyamine conjugates (the larger the polyamine, the slower the migration) versus the oligonucleotide alone. (Gel: 313-97)

C. 3' Terminus Polyamine End Labeled Oligonucleotide, Using a 2'-aminolinker 1. 3' Terminus Polyamine Labeled Oligonucleotide I, Using a 2'-aminolinker Polyamines were attached to the 3'-terminus end of a phosphodiester (2'-OMe) oligonucleotide via a 2'-aminolinker having the sequence F-polyamine [(SEQ ID NO:10)-polyamine] wherein the polyamine is pentaethylenehexamine (oligomer F(i)).

a. Preparation of the Intermediate Linker

The intermediate linker was prepared as described in Example 4-A-1-a, except that a modified cytosine CPG (with a 2'-propylaminolinker) was introduced at the 3' end. The 2'-modification can be prepared by modification of the procedure previously described in application Ser. No. 918, 362 filed Jul. 23, 1992. The CPG containing 2'-ω-phthalimido-propoxy-cytidine was synthesized according to the standard protocols reported in the literature. See, for example, B. S. Sproat and A. I. Lamond, in "Oligonucleotides and Analogues" edited by F. Eckstein, IRL Press at Oxford University Press (1991) p71–72.

b. Preparation of Polyamine Functionalized Oligonucleotide

The polyamine functionalized oligonucleotide was prepared in accordance with Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XVIII.

TABLE XVIII

| Oligomer | Retention Time |
|---|---|
| unreacted F | 28.53 mins |
| Oligomer F(i) | 29.47 mins |

Gel analysis showed progressively slower migration times for the polyamine conjugate versus the oligonucleotide alone. (Gel: 397-85).

2. 3' Terminus Polyamine Labeled Oligonucleotide II, Using a 2'-aminolinker

Polyamines were attached to the 3'-terminus end of a phosphodiester (2'-OMe) oligonucleotide via a 2'-aminolinker having the sequence G-polyamine [(SEQ ID NO:11)-polyamine] wherein the polyamine is pentaethylenehexamine (oligomer G(i)).

a. Preparation of the Intermediate Linker

The intermediate linker was prepared in accordance with the method described in Example 4-A-1-a.

b. Preparation of Polyamine Functionalized Oligonucleotide

The polyamine functionalized oligonucleotide was prepared in accordance with the procedures described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XIX.

TABLE XIX

| Oligomer | Retention Time |
|---|---|
| unreacted G | 28.43 mins |
| oligomer G(i) | 29.06 mins |

Gel analysis showed progressively slower migration times for the polyamine conjugate versus the oligonucleotide alone. (Gel: 397-85)

3. 3' Terminus Polyamine Labeled Oligonucleotide III Using a 2'-aminolinker

Polyamines were attached to the 3'-terminus end of a phosphodiester (2'-OMe) oligonucleotide via a 2'-aminolinker having the sequence H-polyamine [(SEQ ID NO:12)-polyamine] wherein the polyamine is pentaethylenehexamine.

a. Preparation of the Intermediate Linker

The intermediate linker is prepared in accordance with methods described in Example 4-A-1-a.

b. Preparation of Polyamine Functionalized Oligonucleotide

The polyamine functionalized oligonucleotide is prepared in accordance with methods described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XX.

TABLE XX

| Oligomer | Retention Time |
|---|---|
| unreacted H | 28.49 mins |
| oligomer H(i) | 30.36 mins |

Gel analysis showed progressively slower migration times for the polyamine conjugate versus the oligonucleotide alone. (Gel: 397-85)

EXAMPLE 5

Polyamine Labeled 2'-OMe Oligonucleotides and Other RNA Mimics

A. Polyamine Labeled 2'-OMe Oligonucleotide I

Polyamines were attached to the 3'-terminus end of a phosphodiester (2'-OMe) oligonucleotide (via a 3 carbon linker) having the sequence I-polyamine [(SEQ ID NO:13)-polyamine] wherein the polyamine is pentaethylenehexamine (oligomer I(i)).

1. Preparation of the Intermediate Linker

The intermediate linker is prepared in accordance with methods described in Example 4-A-1-a.

2. Preparation of Polyamine Functionalized Oligonucleotide

The polyamine functionalized oligonucleotide is prepared in accordance with methods described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XXI.

TABLE XXI

| Oligomer | Retention Time |
|---|---|
| unreacted I | 28.93 mins |
| oligomer I(i) | 29.59 mins |

Gel analysis showed progressively slower migration times for the polyamine conjugate versus the oligonucleotide alone. (Gel: 353-156)

B. Polyamine Labeled 2'-OMe Oligonucleotide II

Polyamines were attached to the 3'-terminus end of a phosphodiester (2'-OMe) oligonucleotide (via a 6 carbon linker) having the sequence J-polyamine [(SEQ ID NO:13)-polyamine] wherein the polyamine is pentaethylenehexamine (oligomer J(i)).

1. Preparation of the Intermediate Linker

The intermediate linker is prepared in accordance with methods described in Example 4-A-1-a.

2. Preparation of Polyamine Functionalized Oligonucleotide

The polyamine functionalized oligonucleotide is prepared in accordance with methods described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XXII.

TABLE XXII

| Oligomer | Retention Time |
| --- | --- |
| unreacted J | 28.76 mins |
| oligomer J(i) | 29.39 mins |

Gel analysis showed progressively slower migration times for the polyamine conjugate versus the oligonucleotide alone. (Gel: 397-85)

C. Polyamine Labeled 2'-OMe oligonucleotide III

Polyamines were attached to the 3'-terminus end of a phosphodiester (2'-OMe) oligonucleotide (via a 3 carbon linker) having another reporter group(such as biotin, fluorescein) at the other end in the sequence K-polyamine [(SEQ ID NO:7)-polyamine]. Fluorescein at 5' end was added using the required amidite commercially available from Clontech. The polyamine is one of the following pentaethylenehexamine oligomer K(i)

spermine oligomer K(ii)

1. Preparation of the Intermediate Linker

The intermediate linker is prepared in accordance with methods described in Example 4-A-1-a.

2. Preparation of Polyamine Functionalized Oligonucleotide

The polyamine functionalized oligonucleotide is prepared in accordance with methods described in Example 4-A-1-b. The resulting polyamine-oligonucleotide conjugate was characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XXIII.

TABLE XXIII

| Oligomer | Retention Time |
| --- | --- |
| unreacted K | 31.35 mins |
| oligomer K(i) | 31.96 mins |
| oligomer K(ii) | 32.15 mins |

Gel analysis showed progressively slower migration times for the polyamine conjugate versus the oligonucleotide alone. (Gel: 353-149)

EXAMPLE 6

5' Terminus Polyamine End Labeled Oligonucleotide

A. 5'-Terminus Polyamine Oligonucleotide I

Polyamines were attached to the 5'-terminus end of a phosphodiester oligonucleotide having the following sequences:

5'-aminolinker-TCAG (oligomer L)

5'-aminolinker-CGCACGC (oligomer M)

to provide the polyamine oligonucleotides:

5'-polyamine-TCAG (oligomer L(i))

5'-polyamine-CGCACGC (oligomer M(i)) wherein the polyamine is pentaethylenehexamine.

1. Preparation of the Intermediate Linker

The oligonucleotide sequence having a 5'-terminus amino group was synthesized using Aminolink-II(with a six carbon linker) phosphoramidite from Applied Biosystems in the last round of synthesis. The synthesis was conducted with an Applied Biosystems 380B or 994 in the "Trityl-On" mode. The resultant oligonucleotide was cleaved from the solid support and deprotected with concentrated NH40H for 16 hrs at 55° C. Purification on a Sephadex G-25 column yielded a 5'-amino modified oligonucleotide of the specified sequence.

2. Preparation of Polyamine Functionalized Oligonucleotide L(i)

The crude 5'-aminolinker-oligonucleotide (150 O.D. units, approximately 3.75 mmols) was dissolved in freshly prepared $NaHCO_3$ buffer (900 ul, 0.2 M, pH 8.1) and treated with a solution of disuccinimidyl suberate (DSS) (approximately 30 mgs) dissolved in 750 ul of methyl sulfoxide (DMSO). The reaction mixture was left to react for 20 minutes at room temperature. The mixture was divided into three portions and then passed over a Sephadex G-25 column (0.7×45 cm×3columns) to separate the activated oligonucleotide-DSS from the excess DSS. The oligonucleotide-DSS was then frozen immediately and lyophilized to dryness. A solution of polyamine in 0.33 M NaOAc (approximately 60 mL polyamine in 1950 ul 0.33 M NaOAc, pH 5.2, final solution pH 6–8.0) was added to the dried oligonucleotide-DSS, and this mixture was allowed to react overnight at room temperature.

3. Preparation of Polyamine Functionalized Oligonucleotide M(i)

The crude 5'-aminolinker-oligonucleotide (oligomer M) (150 O.D. units, approximately 2.50) was reacted as described in Example 6(b).

4. Characterization of 5' Polyamine Functionalized Oligonucleotides

The resulting polyamine-oligonucleotide conjugates were characterized by reverse phase HPLC and a 20% denaturing gel. Solvent A was 50 mM TEAA, solvent B was $CH_3CN$. The HPLC gradient was from 0–10 mins, 95% solvent A, 5% solvent B; linear increase to 40% solvent B in the next 50 minutes using Water's Delta-Pak C-18 reverse phase column. HPLC retention times were as set forth in Table XXIV.

TABLE XXIV

| Oligomer | Retention Time |
| --- | --- |
| unreacted L | 22.78 mins |
| oligomer L(i) | 28.27 mins |
| unreacted M | 24.50 mins |
| oligomer M(i) | 26.72 mins |

EXAMPLE 7

Preparation of a Reactive Site Containing Oligonucleotide

An oligonucleotide having the sequence TGGGAGC-CATAGCGAGGUCT (SEQ ID NO: 14) is treated with uracil DNA glycosylase followed by T4 endonuclease. The product is then treated with 1-phthalimidobutyl-4-thiol. Nucleophilic attack by the thiol with the protected aminobutyl moiety results in addition to what was the 3' position of the opened nucleotide. Treatment of this composition with hydrazine will deblock the phthalimide yielding an amino species which is then treated with bifunctional linker followed by treatment with an appropriate polyamine species as per Example 4-A-1-b.

EXAMPLE 8
Preparation of Polyamine Conjugated Oligonucleotide

An oligonucleotide is prepared as described in Example 7 treating the product with NH—CH—CH$_2$—SH. The thiol group will attack the double bond of the opened nucleotide. The resulting amine may then be further derivatized with a reactive group.

EXAMPLE 9
Thermodynamic Parameters of Oligoamine-Oligonucleotide Conjugates with DNA and RNA Targets The ability of the functionalized oligonucleotides of the invention to hybridize to their complementary RNA or DNA sequences is determined by thermal melting analysis. The RNA complement is synthesized from T7 RNA polymerase and a template-promoter of DNA synthesized with an Applied Biosystems, Inc. 380B nucleic acid synthesizer. The RNA species is purified by ion exchange using FPLC (LKB Pharmacia, Inc.) or by denaturing urea-PAGE. Natural antisense oligonucleotides or those containing functionalization at specific locations are added to either the RNA or DNA complement at stoichiometric concentrations to form hybrid duplexes. The absorbance (260 nm) hyperchromicity dependence on temperature upon duplex to random coil transition is monitored using a Gilford Response II spectrophotometer. These measurements are performed in a buffer of 10 mM Na-phosphate, pH 7.4, 0.1 mM EDTA, and NaCl to yield an ionic strength of either 0.1 M or 1.0 M. Data are analyzed by a graphic representation of $1/T_m$ vs ln[Ct], where [Ct] is the total oligonucleotide concentration. From this analysis the thermodynamic parameters are determined. Based upon the information gained concerning the stability of the duplex or hetero-duplex formed, the placement of the polyamines into oligonucleotides is assessed for its effects on helix stability. Modifications that drastically alter the stability of the hybrid exhibit reductions or enhancements in the free energy (delta G) and decisions concerning their usefulness in antisense oligonucleotides are made.

EXAMPLE 10
Conjugation of Polyamines to Abasic Site-Containing Oligonucleotides To 15.2 ODS of an abasic oligonucleotide (SEQ ID NO: 4) in 100 μl water was added 25 μl 1M NaOAc (pH 5.0) solution. The final concentration of the acetate buffer was 0.2 M. 5.3 mg of triethylenetetramine was dissolved in 500 μl of 1M NaOAc (pH 5.0) solution. 50 μl of the resulting solution was added to the oligonucleotide solution followed by 50 μl of NaCNBH$_3$ (57 MM solution). The pH of the resulting solution was below 8.0. The solution was vortexed and left to stand overnight. HPLC and Gel analysis indicated conjugation of the triethylenetetramine to the oligonucleotide. The conjugated oligonucleotide was purified by G-25 and HPLC. HPLC retention times are set forth in Table XXVI.

TABLE XXVI

| Oligomer | Retention time (mins) |
| --- | --- |
| parent oligonucleotide (SEQ ID NO: 3) | 26.66 |
| abasic oligonucleotide (SEQ ID NO: 4) | 26.16 |
| (SEQ ID NO: 4)-triethylenetetramine conjugate | 26.04 |

EXAMPLE 11
Oligonucleotide Synthesis

Oligonucleotides of the following sequences were synthesized with an Applied Biosystems 380B or 994 in the "Trityl On" mode. The resultant oligonucleotides were cleaved from the solid support and deprotected with concentrated NH$_4$OH for 16 hour at 55° C. HPLC purification with a Water's Delta-Pak C-18, reverse phase column followed with the given gradient: Solvent A: 50 mM TEAA, pH=7.4; Solvent B: CH$_3$CN; 0–10 mins., 95% A, 5% B; linear increase to 60% B in the next fifty mins. The full-length, DMT-on oligonucleotide was separated from the impurities. Treatment with 80% acetic acid removed the DMT. A final run over a Sephadex G-25 column yielded pure oligonucleotides of the specified sequences.

CGC AGU CAG CC (SEQ ID NO:3)
GAU CT (SEQ ID NO:15)

TABLE XXV

| | DNA TARGET | | | RNA TARGET | | |
| --- | --- | --- | --- | --- | --- | --- |
| Oligomer | $T_m$(° C.) | $\Delta T_m$(° C.) | $\Delta\Delta G°_{37°C.}$ | $T_m$(° C.) | $\Delta T_m$(° C.) | $\Delta\Delta G°_{37°C.}$ |
| wild type oligomer D | 60.6 | — | — | 64.9 | — | — |
| oligomer D | 60.3 | −0.3 | +0.3 | 64.6 | −0.3 | 0.0 |
| oligomer D + 5'-6-carbon amino linker) | 60.8 | +0.2 | 0.0 | 65.1 | +0.2 | 0.0 |
| oligomer E | 60.8 | +0.2 | −0.8 | 65.8 | +0.9 | −1.0 |
| oligomer E(i) | 61.2 | +0.6 | −1.4 | 66.3 | +1.4 | −1.9 |
| oligomer E + spermine | 61.5 | +0.9 | −1.7 | 67.1 | +2.2 | −2.1 |
| oligomer E(ii) | 61.2 | +0.6 | −1.3 | 67.5 | +2.6 | −2.6 |

EXAMPLE 12

Abasic Site Generation

To generate an abasic site at the uracil position in the sequences prepared in Example 11, uracil DNA glycosylase was added to the oligonucleotides (approximate ratio 100 O.D. oligonucleotide to 100 "units" enzyme). This was left to react overnight at room temperature. HPLC analysis (HPLC gradient was as follows: Solvent A:50 mM TEAA, pH=7.4; Solvent B: $CH_3CN$; 0–10 mins., 95% A, 5% B; linear increase to 15% B in the next fifty mins. HPLC column: Water's Delta-Pak C-18, reverse phase) shows a small excess uracil peak at 2.58 minutes and the oligonucleotides with the abasic site at 33.38 minutes.

CGC AGN CAG CC (SEQ ID NO:4)
GAN CT (SEQ ID NO:16)
(N=abasic site)

EXAMPLE 13

Conjugation to Oligonucleotides Containing Abasic Sites

A. Oligonucleotide Having SEQ ID NO:4.

The oligonucleotide having sequence CGC AGN CAG CC (SEQ ID NO:4) was divided into 25 O.D. unit samples for conjugation. A 50 µl portion of 1M NaOAc was added to each of these samples (25 O.D./100 µl of HPLC grade water) to assure a low pH. The following solutions were made:

TABLE XXVII

| Ligand | mg/ul (pH = 5.0) | 1 M NaOAc | DMF |
|---|---|---|---|
| 6-((biotinoyl)amino) caproic acid hydrazide | 5 mg | 300 µl | 100 µl |
| fluorescein-5-thiosemicarbazide | 5 mg | 200 µl | 100 µl |
| Lys—Tyr—Lys (tripeptide) | 5 mg | 200 µl | |
| Lys—Trp—Lys (tripeptide) | 5 mg | 200 µl | |
| triethylenetetramine (TEA) | 5 mg | 200 µl | |
| pentaethylenehexamine (PEHA) | 5 mg | 200 µl | |
| 5-amino-O-phenanthroline | 5 mg | 200 µl | 100 µl |
| 1-pyrene-butyryl-hydrazide | 5 mg | 200 µl | 100 µl |
| PEG-hydrazide (methoxy polyestylene glycol-carboxymethyl hydrazide) | 5 mg | 200 µl | |

A 100 µl portion of each of the solutions given in Table XXVII was added to the oligonucleotide solutions; 5 mgs of PEG-hydrazide were added directly. After about period of 15 minutes, 100 µl of a $NaCNBH_3$ solution (0.20 M $NaBH_3CN$ in 0.25 M NaOAc) was added to each of the reactions. The reaction mixtures were then put on a vortex-shaker and left overnight at room temperature. The conjugates were then analyzed by HPLC and 20% PAGE gel, indicating formation of the conjugate. The results are shown in Table XXVIII.

TABLE XXVIII

| Oligo./Conjugate | HPLC Program | Retention Time (min.) | Yield (O.D.) |
|---|---|---|---|
| SEQ ID NO:3 | biohr | 33.09 | |
| SEQ ID NO:4 | biohr | 31.55 | |
| SEQ ID NO:4 + biotin | biohr | 40.51 | 7.5 |
| SEQ ID NO:4 + fluorescein | biohr | 46.81 | 1.6 |
| SEQ ID NO:4 + Lys—Trp—Lys | biohr | 36.66 | 6.1 |
| SEQ ID NO:4 + o-phenanthroline | biohr | 36.66 | 19.1 |
| SEQ ID NO:4 + pyrene | biohr | 54.29 | 23.2 |
| SEQ ID NO:4 + TEA | biohr | 31.81 | 5.9 |
| SEQ ID NO:3 | anal. | 17.59 | |
| SEQ ID NO:4 | anal. | 17.30 | |
| SEQ ID NO:4 + PEHA | anal. | 17.34 | 1.8 |

TABLE XXVIII-continued

| Oligo./Conjugate | HPLC Program | Retention Time (min.) | Yield (O.D.) |
|---|---|---|---|
| SEQ ID NO:4 + Lys—Tyr—Lys | anal. | 17.37 | 8.6 |
| SEQ ID NO:4 + PEG | anal. | 36.00 | 9.3 |

The "biohr" HPLC gradient was as follows: Solvent A: 50 mM TEAA, pH=7.4; solvent B: $CH_3CN$; 0–10 mins., 95% A, 5% B; linear increase to 15% B in the next fifty mins. HPLC column: Water's Delta-Pak C-18, reverse phase. The "anal." HPLC gradient was as follows: Solvent A: 50 mM TEAA, pH=7.4; Solvent B: $CH_3CN$; 0–10 mins.,95% A, 5% B; linear increase to 60% B in the next fifty mins. HPLC column: Water's Delta-Pak C-18, reverse phase.

B. Oligonucleotide Having SEQ ID NO:16.

The oligonucleotide having sequence GANCT (Seq. ID No. 16) (40 ODS) was treated in 100 µL of 1M NaOAC solution followed by 10 mg of 5-amino-O-phenanthroline dissolved in 200 µL of 1M NaOAC. After about 15 mts., 100 µL of a $NaCNBH_3$ solution (0.2M $NaBH_3CN$ in 0.25M NaOAC) was added to the reaction and allowed to stand overnight. The conjugate was purified by size exclusion and reverse-phase HPLC.

TABLE XXIX

| HPLC Data | | HPLC program | Retention Time (min.) |
|---|---|---|---|
| SEQ ID NO: 15 | I-6839 | biohr | 32.39 |
| SEQ ID NO: 16 | I-6839-D | biohr | 27.25 |
| | I-6839-OP | biohr | 47.87 |

The NMR spectra show the formation of the abasic site and the conjugate between phenathroline ligand and the pentamer oligonucleotide. The final product is a homogeneous single product with no DNA fragmentation or 1,4-addition products evidenced.

$^1$H NMR analysis showed the following peaks: In the case of 6839 and 6839D, peaks between 7.4 and 8.4; whereas in 6839-OP peaks between 7.0 and 8.8 (protons from O-phenanthroline). In other words, 6839-OP conjugate showed the combination spectrun of Sequence 16 and O-phenanthroline. In $^{31}$ NMR dispersion of signals was higher for the conjugate (−0.7 to 0.4 ppm) than the Sequence 16.

EXAMPLE 14

To further derivatize the oligonucleotide-polyamine conjugate, imidazole-4-acetic acid is attached to the free amines made available by the polyamines attached in Example 4-A-4-b.

Imidazole-4-acetic acid is treated with 2,4-dinitrofluorobenzene. The product is treated with pentafluorophenol/DCC to give the active ester of imidazole-4-acetic acid, which is also protected in the imidazole ring by a DNP group (Compound 13).

The oligonucleotide-polyamine conjugate is reacted with Compound 13 in 0.2M $NaHCO_3$ buffer/DMF. The product, oligonucleotide-polyimidazole conjugate, then is treated with mercapto ethanol to remove the DNP group, and then is purified by size exclusion and HPLC methods.

What is claimed is:

1. A method for detecting the presence or absence of an RNA in a biological sample suspected of containing said RNA comprising:

contacting a sample with a compound having the structure:

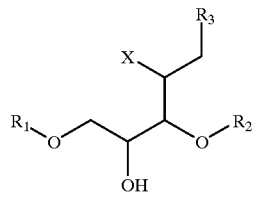

wherein $R_1$ and $R_2$ are independently H, a nucleotide, oligonucleotide or polyamine species and at least one of $R_1$ and $R_2$ is a purine containing oligonucleotide, $R_3$ is a linear or cyclic non-aromatic polyamine species, and X is H, O—$R_{11}$, S—$R_{11}$, F, Cl, Br, CN, $CF_3$, $OCF_3$, OCN, $SOCH_3$, $SO_2CH_3$, $ONO_2$, $N_3$, $HN_2$, heterocylcoalkyl, heterocycloalkaryl, aminoalkylamino, polyalkylamino, substituted silyl, a reporter molecule, an RNA cleaving group, wherein $R_{11}$ is H, $C_1$ to $C_{10}$ straight or branched chain lower alkyl or substituted lower alkyl, $C_2$ to $C_{10}$ straight or branched chain lower alkenyl or substituted lower alkyenyl, $C_3$ to $C_{10}$ straight or branched chain lower alkynyl or substituted lower alkynyl, a $^{14}C$ containing lower alkyl, lower alkenyl or lower alkynyl, $C_7$ to $C_{14}$ substituted or unsubstituted alkaryl or aralkyl, a $^{14}C$ containing $C_7$ to $C_{14}$ alkaryl or aralkyl, alicyclic, heterocyclic, a reporter molecule, a RNA cleaving group; said compound being specifically hybridizable with said RNA; and detecting the presence or absence of hybridization of the compound to the sample wherein hybridization is indicative of the presence of RNA in the sample.

2. The method of claim 1 wherein said compound further includes one or more of reporter groups, alkylating agent, intercalating agents, cell receptor binding molecules, steroids, peptides, crown amines, porphyrins, or cross-linking agents attached to said polyamine.

3. The method of claim 1 wherein $R_1$ and $R_2$, taken together range from about 8 to about 50 nucleotide bases in length.

4. The method of claim 1 wherein $R_1$ and $R_2$ taken together range from about 12 to about 20 nucleotide bases in length.

* * * * *

UNITED STATES PATENT AND TRADEMARK OFFICE
CERTIFICATE OF CORRECTION

PATENT NO. : 6,495,671 B1
DATED : December 17, 2002
INVENTOR(S) : Muthiah Manoharan et al.

It is certified that error appears in the above-identified patent and that said Letters Patent is hereby corrected as shown below:

Title page,
Item [56], References Cited, OTHER PUBLICATIONS, "Friedberg", reference, "pp. 153," please insert -- 189 , --; "Inoue", reference, please delete "(15(15)" and insert therefor -- 15(15) --; "Lemaitre", please insert -- Stomatitis -- between "vesicular" and "Virus"; "Manoharan", please delete "⁻C" and insert therefor -- $^{13}$C --; "Poec'h", reference, please delete "Oligonucleotides" and insert therefor
 -- Oligodeoxynucleotides --; "Sawai", reference, please delete "2'-5'-Oligoadenylates" and insert therefor -- 2',5'-Oligoadenylates --; "Smith-Jones", reference, after "4'-
[ "please insert -- ( --; "Vasseur", reference, please delete "Ascite" and insert therefor
 -- Abasic --.

Signed and Sealed this

Twenty-seventh Day of July, 2004

JON W. DUDAS
*Acting Director of the United States Patent and Trademark Office*